(12) United States Patent
Ruan

(10) Patent No.: US 10,849,934 B2
(45) Date of Patent: Dec. 1, 2020

(54) COMPOUND AND PREPARATION METHOD THEREOF

(71) Applicant: GUANGXI JIUFU BIOTECHNOLOGY CO., LTD, Guangxi (CN)

(72) Inventor: Jun Ruan, Guangxi (CN)

(73) Assignee: GUANGXI JIUFU BIOTECHNOLOGY CO., LTD, Nanning (CN)

( * ) Notice: Subject to any disclaimer, the term of this patent is extended or adjusted under 35 U.S.C. 154(b) by 0 days.

(21) Appl. No.: 16/808,371

(22) Filed: Mar. 4, 2020

(65) Prior Publication Data

US 2020/0199144 A1   Jun. 25, 2020

Related U.S. Application Data

(63) Continuation-in-part of application No. PCT/CN2018/115649, filed on Nov. 15, 2018.

(30) Foreign Application Priority Data

Sep. 22, 2017   (CN) .......................... 2017 1 0868177

(51) Int. Cl.
| | | |
|---|---|---|
| *A61K 35/618* | (2015.01) | |
| *A61P 25/36* | (2006.01) | |
| *A61K 31/575* | (2006.01) | |
| *A23L 33/105* | (2016.01) | |
| *A23L 33/10* | (2016.01) | |
| *A23L 33/00* | (2016.01) | |
| *C07D 493/08* | (2006.01) | |
| *C07J 9/00* | (2006.01) | |

(52) U.S. Cl.
CPC ............ *A61K 35/618* (2013.01); *A23L 33/00* (2016.08); *A23L 33/10* (2016.08); *A23L 33/105* (2016.08); *A61K 31/575* (2013.01); *A61P 25/36* (2018.01); *C07D 493/08* (2013.01); *C07B 2200/13* (2013.01); *C07J 9/00* (2013.01); *Y02P 20/54* (2015.11)

(58) Field of Classification Search
CPC .................................................. C07D 493/08
See application file for complete search history.

(56) References Cited

U.S. PATENT DOCUMENTS

| | | | |
|---|---|---|---|
| 2006/0204601 A1 | 9/2006 | Palu et al. | |
| 2010/0048457 A1* | 2/2010 | Xie .......................... | A61P 11/00 514/1.1 |
| 2010/0209542 A1 | 8/2010 | Boyer et al. | |
| 2019/0151375 A1* | 5/2019 | Ruan ..................... | A61K 35/618 |
| 2020/0199144 A1* | 6/2020 | Ruan ..................... | C07D 493/08 |

FOREIGN PATENT DOCUMENTS

| | | | |
|---|---|---|---|
| CN | 1562087 A | 1/2005 | |
| CN | 1796400 A | 7/2006 | |
| CN | 102627682 A | 8/2012 | |
| CN | 102631371 A | 8/2012 | |
| CN | 102697814 A | 10/2012 | |
| CN | 103450310 A | 12/2013 | |
| CN | 103610699 A | 3/2014 | |
| CN | 106146596 A | 11/2016 | |
| CN | 106800580 A | 6/2017 | |
| CN | 107865889 A | 4/2018 | |
| CN | 107865890 A | 4/2018 | |
| CN | 109646562 A * | 4/2019 | |
| WO | 2018059241 A1 | 4/2018 | |
| WO | WO-2019057220 A1 * | 3/2019 | .............. A61P 25/36 |
| WO | WO-2019057221 A1 * | 3/2019 | ............ A23L 33/105 |
| WO | WO-2019057222 A1 * | 3/2019 | .............. A23L 33/00 |
| WO | WO 2020114096 * | 6/2020 | ............ C07D 493/08 |

OTHER PUBLICATIONS

Chen; Zhong yao cai = Zhongyaocai = Journal of Chinese Medicinal Materials 2004, 27, 125-127. Abstract. (Year: 2004).*
Latif; "Isolation of Natural Products by Preparative High Performance Liquid Chromatography (Prep-HPLC)" In: Sarker S., Nahar L. (eds) Natural Products Isolation. Methods in Molecular Biology (Methods and Protocols), 2012, vol. 864. Humana Press. doi: 10.1007/978-1-61779-624-1_10 (Year: 2012).*
Liang; International Immunopharmacology 2018, 54, 210-220. doi: 10.1016/j.intimp.2017.11.004 (Year: 2018).*
Wheat; Science 1960, 132, 1310-1311. DOI: 10.1126/science.132. 3436.1310 (Year: 1960).*
Unverified Machine Translation of Patent CN 102697814A . (Year: 2012).*
Unverified Machine Translation of Patent CN 102631371A. (Year: 2012).*
Unverified Machine Translation of Patent CN 103610699A. (Year: 2014).*
Unverified Machine Translation of Patent WO 2019057220. (Year: 2019).*
International search report of PCT Patent Application No. PCT/CN2018/115649 dated Feb. 14, 2019.
Ning Zhu et al., The Lipids of Slugs and Snails: Evolution, Diet and Biosynthesis, Lipids, 1994, pp. 869-875, vol. 29, No. 12.
Jordi Folch et al., A Simple Method for the Isolation and Purification of Total Lipides from Animal Tissues, The Journal of Biological Chemistry, May 1957, pp. 497-509, vol. 226.
Genlin Chen, The Pharmacological Research Progress of Limax, Journal of North Pharmacy, Oct. 1, 2013, pp. 55-56, vol. 10, No. 10.

(Continued)

*Primary Examiner* — Daniel R Carcanague

(57) ABSTRACT

Disclosed is a compound, prepared by extracting and separating from Limax. Also disclosed is a method for extracting and separating the compound, which is simple and easy to operate. The compound has sedative and hypnotic effects, and has significant effects on physiological or psychological dependent detoxification or detoxication. It has potential application value for preparing detoxification or detoxication drugs, and provides new ideas for the further development of detoxification drugs.

7 Claims, 7 Drawing Sheets

(56) References Cited

OTHER PUBLICATIONS

Xia Cai et al., Study on the Optimum Extraction Process of Limax Polysaccharide, Guide of China Medicine, Dec. 15, 2008, pp. 253-255, vol. 6, No. 23.

Juan Wang, Screen the Effective Extraction of Limax against Lung Carcinoma and Investigation of its Activity, University of South China Master's Thesis, Dec. 31, 2014, pp. 10-12.

Hai Xiang et al. Managing editor, The Process Technology of Rice Bran, China Light Industry Press, Apr. 30, 2014, pp. 191-192.

Yong Liu et al. Managing editor, The Traditional Chinese Medicine Resource of Jiangxi, Science and Technology of China Press, Dec. 31, 2015, p. 855.

International search report of PCT Patent Application No. PCT/CN2017/101679 dated Dec. 28, 2017.

Zhao Wang et al., Pharmacological Study of Limax Extract on Inhibiting H14 Cell, Zhong Yao Cai, Jan. 2004, pp. 33-35, vol. 27, No. 1.

Hidayat Hussain et al., Chemistry and Biology of the Genus Voacanga, Pharmaceutical Biology, pp. 1183-1193, 2012, vol. 50, No. 9.

M. D. Garcia et al., Topical Antiinflammatory Activity of Phytosterols Isolated from Eryngium Foetidum on Chronic and Acute Inflammation Models, Phytotherapy Research, 1999, pp. 78-80, vol. 13.

European Food Safety Authority, Scientific Opinion on the Safety of Stigmasterol-rich Plant Sterols as Food Additives, EFSA Journal, 2012, pp. 1-39, vol. 10, No. 5.

T. Itoh et al., Sterol Composition of 19 Vegetable Oils, Journal of the American Oil Chemists Society, Apr. 1973, pp. 122-125, vol. 50.

M. I. P. Kovacs et al., A Simple Method for the Determination of Cholesterol and Some Plant Sterols in Fishery-based Food Products, Journal of Food Science, 1979, vol. 44.

Office Action of counterpart Canadian Patent Application No. 3,033,547 dated Apr. 15, 2020.

\* cited by examiner

COMPOUND AND PREPARATION METHOD THEREOF

CROSS REFERENCE TO RELATED APPLICATIONS

This application is a continuation-in-part application of PCT/CN2018/115649, filed on Nov. 15, 2018, which claims priority of China patent application No. 201710868177.7 filed on Sep. 22, 2017. The contents of the above applications are all hereby incorporated by reference.

TECHNICAL FIELD

The present invention belongs to the field of biomedical chemistry, and particularly relates to a compound and a preparation method thereof.

BACKGROUND

Limax, also known as slug, is a dry whole body of *Vaginulus alte* (Ferussac), a Vaginulus animal; Vaginulalte (Ferussac). From the perspective of Chinese Medicine: it is salty and cold; acting in the lung meridian, the liver meridian, and the large intestine meridian. It has effects of expelling wind for relieving convulsion, clearing away heat and removing toxic substances, and reducing swelling and alleviating pain; it is mainly used for treating crooked eye and mouth due to apoplexy, tendon and vessel contracture, infantile convulsion, wheeze, pharyngeal swelling, sore throat, carbuncle, erysipelas, sucutaneous nodule, swelling and pain due to hemorrhoid, and proctoptosis. It has effects of clearing away pyretic toxicity, regulating respiratory passage, and dredging blood vessels; it is mainly used for treating pharyngitis, asthma, proctoptosis, hernia, carbuncle, amenorrhea, and centipete bite.

Existing technology has extensively researched the antibacterial and anticancer aspects of Limax. At present, it has been found that, the Chinese medicine Limax extract has significant sedative and hypnotic effects, has a certain inhibitory effect on morphine and amphetamine-induced excitability in mice, and has detoxification treatment effect on withdrawal symptoms in morphine-dependent rats, with safe acute toxicity, no physiological or psychological dependence. Hence, if the detoxification substances in the Limax extract can be further studied and the characteristics can be clarified, it would be of great significance for the further development of Chinese medicine detoxification products.

SUMMARY

One object of the present invention is to provide a compound, which provides a new idea for the research and development of Chinese medicine detoxification products.

The present invention adopts the following technical solutions:

A compound having a structure of

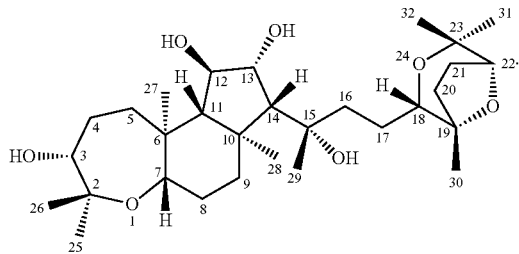

Further, the compound has a molecular formula: $C_{30}H_{52}O_7$; molecular weight: 524; melting point: 248-249° C.; solubility: white needle-like or columnar crystal, insoluble in water, insoluble in acid and alkali, easily soluble in methanol and acetone, soluble in ethanol, ethyl acetate, hot trichloromethane, and slightly soluble in cold trichloromethane; the chiral C configurations includes: C3, R; C6, S; C7, S; C10, S; C11, R; C12, R; C13, R; C14, R; C15, S; C18, S; C19, S; and C22, R.

Further, the compound is prepared by extracting and separating from Limax.

Furthermore, the Limax includes one or more of *Vaginulus alte* (Ferussac), *Limax maximus* L., *L. flavus* L., *Agriolimax agrestis* L., and *Phiolomycus bilineatus*.

A method for preparing the compound as described above, including the following steps:

S1. pulverizing Limax to obtain Limax powder;

S2. putting the Limax powder into a supercritical $CO_2$ extractor for extraction to obtain an extract;

S3. adding the extract, potassium hydroxide, and water to a reactor in a weight ratio of "extract:potassium hydroxide:water=1:1:1.5", mixing evenly, and heating and stirring to produce a saponification reaction to obtain a reaction solution A;

S4. adding the reaction solution A to an organic solvent for extraction, separating the organic solvent layer, washing with water until the water washed solution becomes neutral, separating the organic solvent layer, and recovering the organic solvent under reduced pressure to obtain a thick paste A;

S5: adding methanol to thick paste A, heating to dissolve, filtering, leaving a filtrate to cool, standing, crystallizing, and reserving a mother liquor for later use; and S6: subjecting the crystals to preparative medium-pressure liquid phase separation to obtain the compound; wherein the liquid phase conditions are as follows: reversed-phase C18 column, solvent system: methanol:acetonitrile:isopropanol:water (70:20:6:4), and flow rate: 50 ml/min.

Further, for the above-mentioned compound, the conditions for the supercritical $CO_2$ extraction of step S2 include: pressure: 25 KPa, temperature: 65° C., flow: 400-500 PV, and extraction time: 4 h; the organic solvent of step S4 includes one or two of ethyl ether, ethyl acetate and n-butanol.

A method for preparing the compound as described above, including the following steps:

T1. pulverizing Limax to obtain Limax powder;

T2. putting the Limax powder into a multi-functional extraction tank, adding an organic menstruum for reflux extraction, filtering, and recovering the organic menstruum from the extraction solution under reduced pressure to obtain a thick paste B;

T3. adding thick paste B, potassium hydroxide and water to the reactor in a weight ratio of "extract:potassium hydroxide:water=1:1:1.5", mixing evenly, and heating and stirring to produce a saponification reaction to obtain a reaction solution B;

T4. adding the reaction solution B to an organic solvent for extraction, separating an organic solvent layer, washing with water until the water washed solution becomes neutral, separating the organic solvent layer, and recovering the organic solvent under reduced pressure to obtain a thick paste C;

T5: adding methanol to thick paste C, heating to dissolve, filtering, leaving a filtrate to cool, letting it stand, crystallizing, and reserving a mother liquor for later use; and T6: subjecting the crystals to preparative medium-pressure liquid phase separation to obtain the compound; the liquid phase condition being: reversed-phase C18 column, solvent system: methanol:acetonitrile:isopropanol:water (70:20:6:4), and flow rate: 50 ml/min.

Further, the method for preparing the compound as described above, wherein the organic menstruum comprises one or two of n-hexane, ethanol, methanol, acetone, trichloromethane, oil, gasoline, petroleum ether, n-butanol, ethyl ether, and ethyl acetate.

A method for preparing the compound as described above, further comprising the following steps: taking the mother liquor of S5 or T5, adding water in a ratio of methanol:water (8:2), heating under reflux, and separating a black oil, filtering with the methanol solution, recovering the methanol, drying, and adding trichloromethane into the residue, heating to dissolve, cooling, standing to precipitate crystals, and filtering to obtain the crystals; washing with a small amount of trichloromethane, drying, adding methanol, heating to dissolve, cooling, precipitating crystals, filtering, and drying to obtain the compound.

The compound of the present application is obtained from the traditional Chinese medicine Limax by a simple method. The compound has sedative and hypnotic effects, and has significant effects on physiological or psychological dependent detoxification or detoxication. It has potential application value for preparing detoxification or detoxication drugs.

DETAILED DESCRIPTION

I A Compound

Example 1

The present invention provides a compound having a specific structure of:

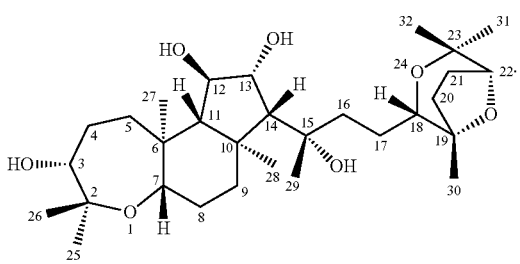

Figure 1:
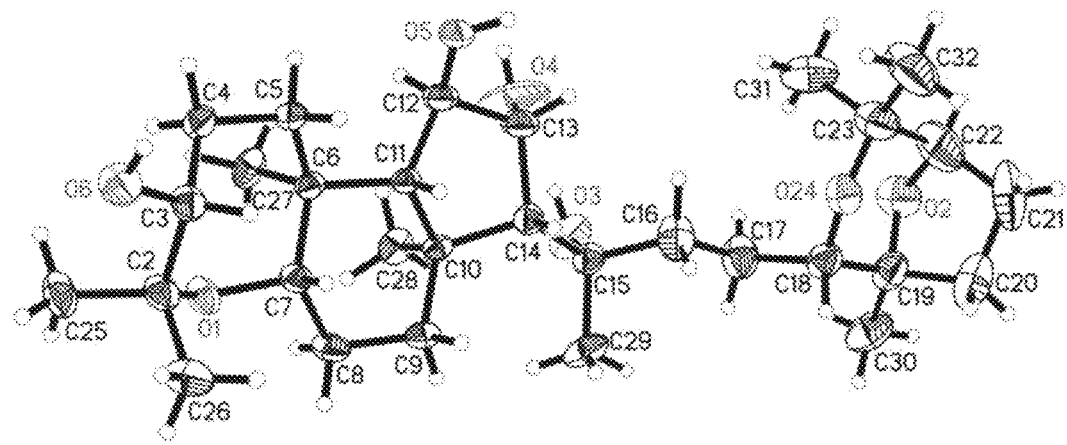
FIG. 1 shows an X-ray crystal structure of the compound of the present application.
Figure 2:
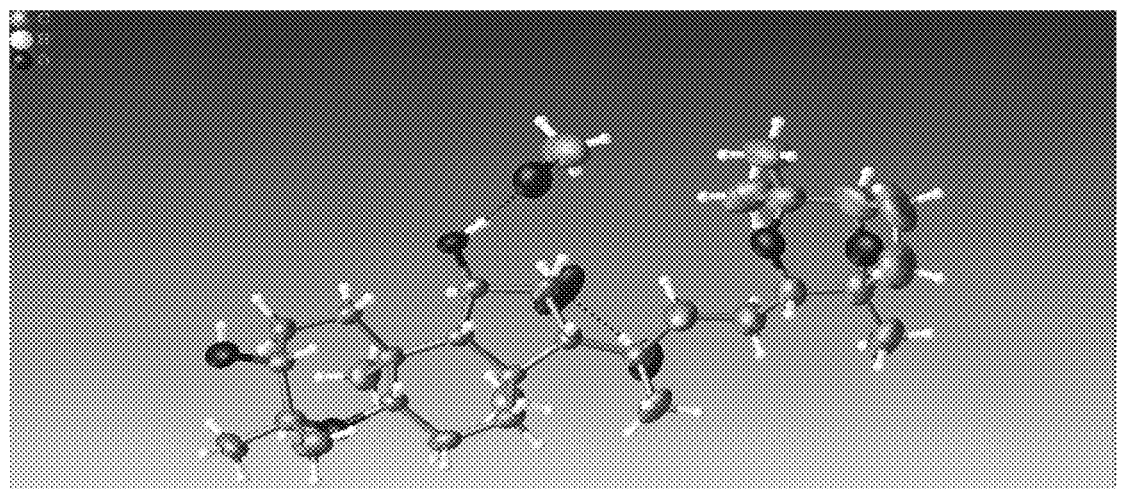
FIG. 2 is a crystal space stereostructural diagram of the compound of the present application.
Figure 3:
FIGS. 3 and 4 are crystal forms of the compound of the present application.
Figure 4:
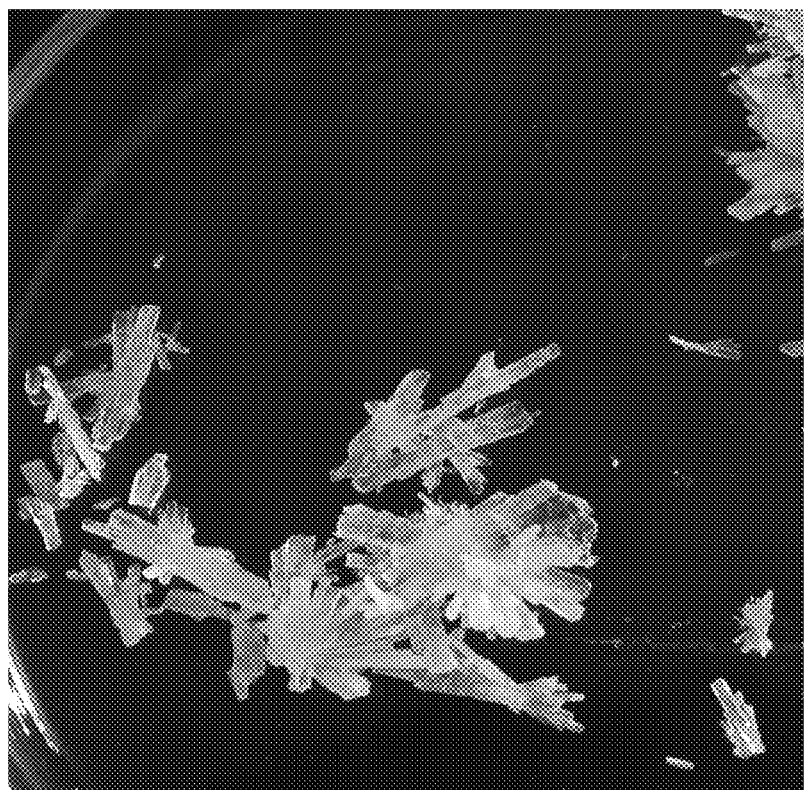
Figure 5:
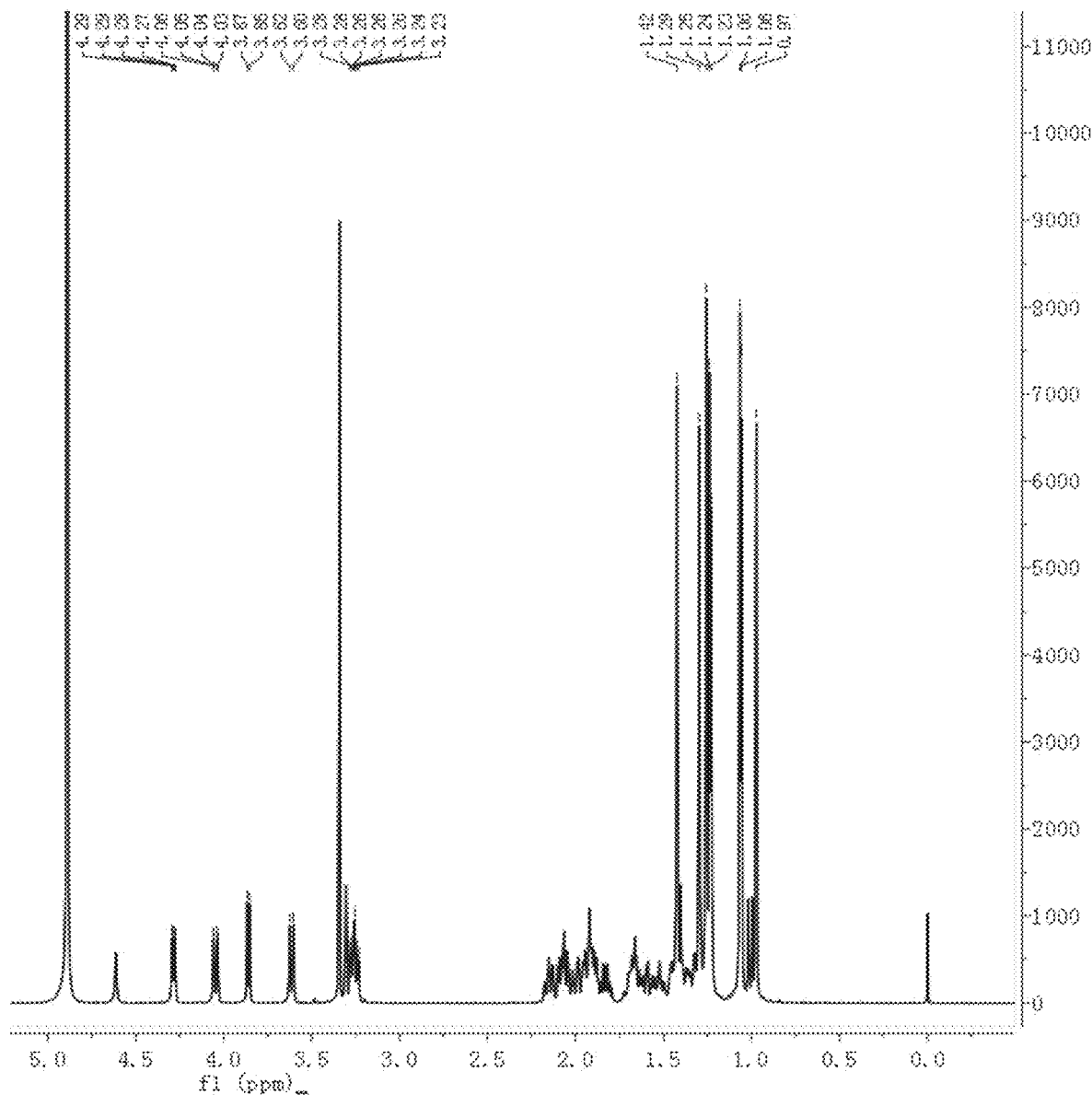
FIG. 5 shows hydrogen (H) NMR spectra (500 MHz, in CD$_3$OD) of the compound of the present application.
Figure 6:
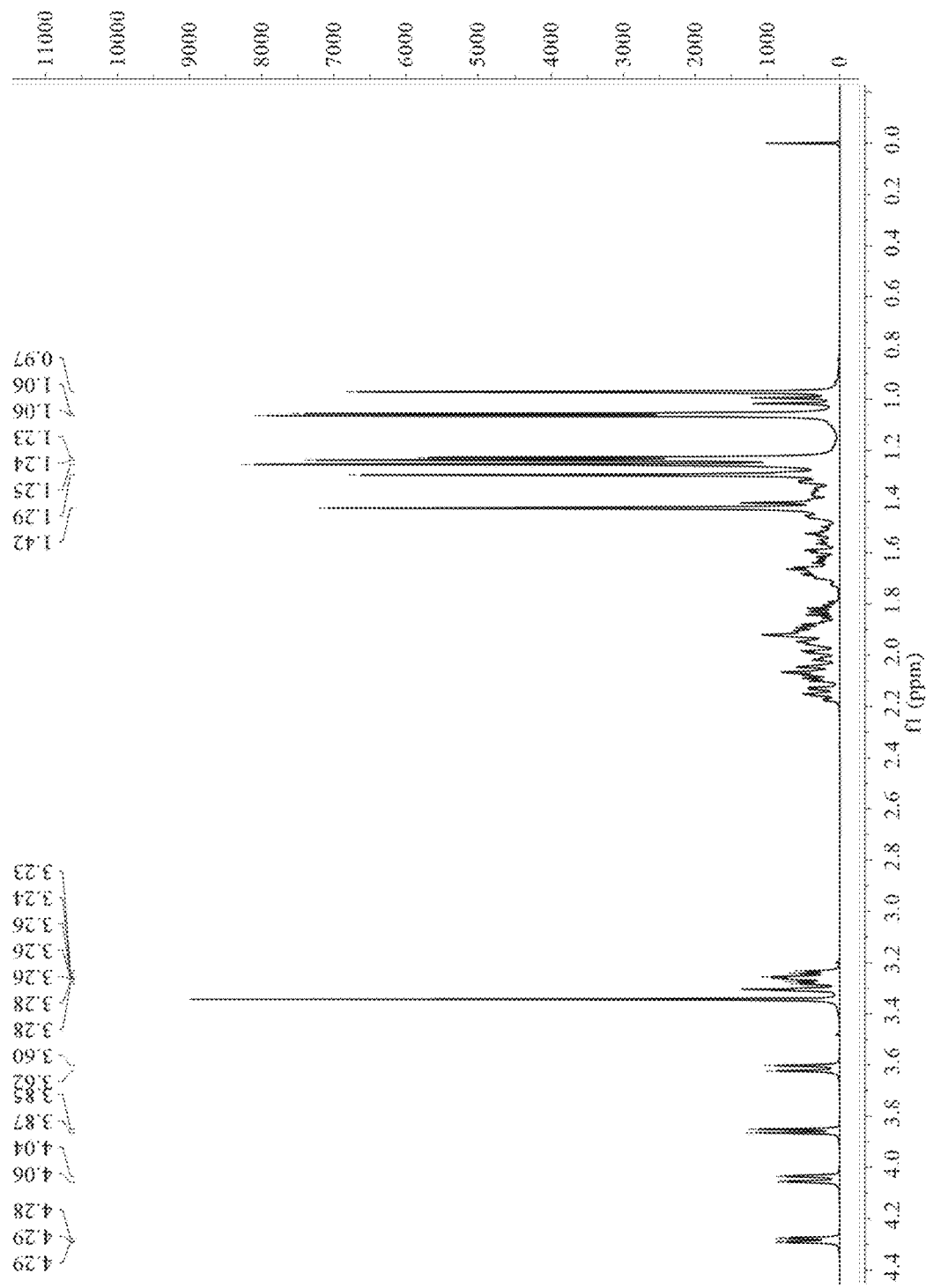
FIG. 6 shows a partial enlarged view of FIG. 5.
Figure 7:
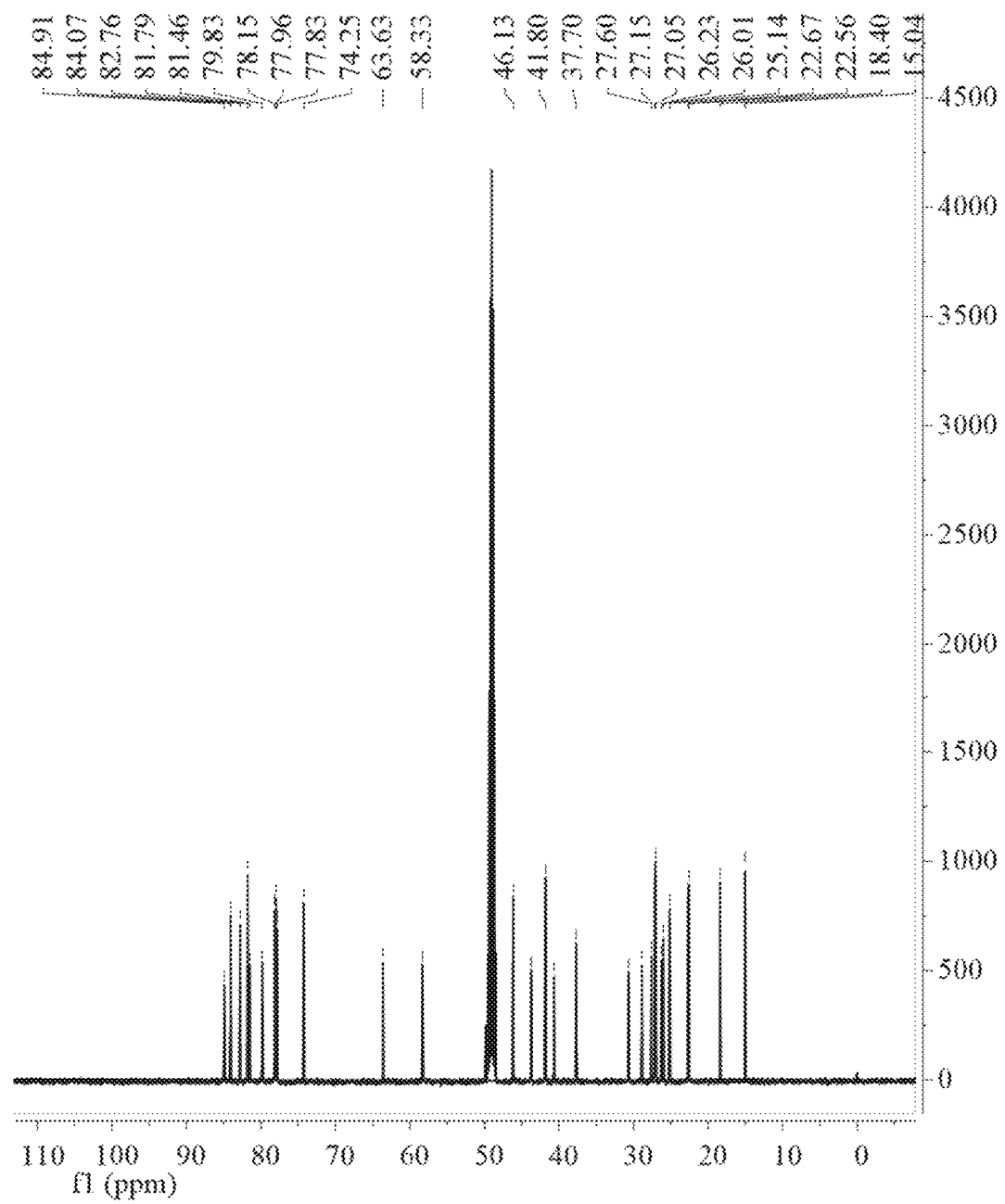
FIG. 7 shows carbon (C) NMR spectra (500 MHz, in CD$_3$OD) of the compound of the present application.
Figure 8:
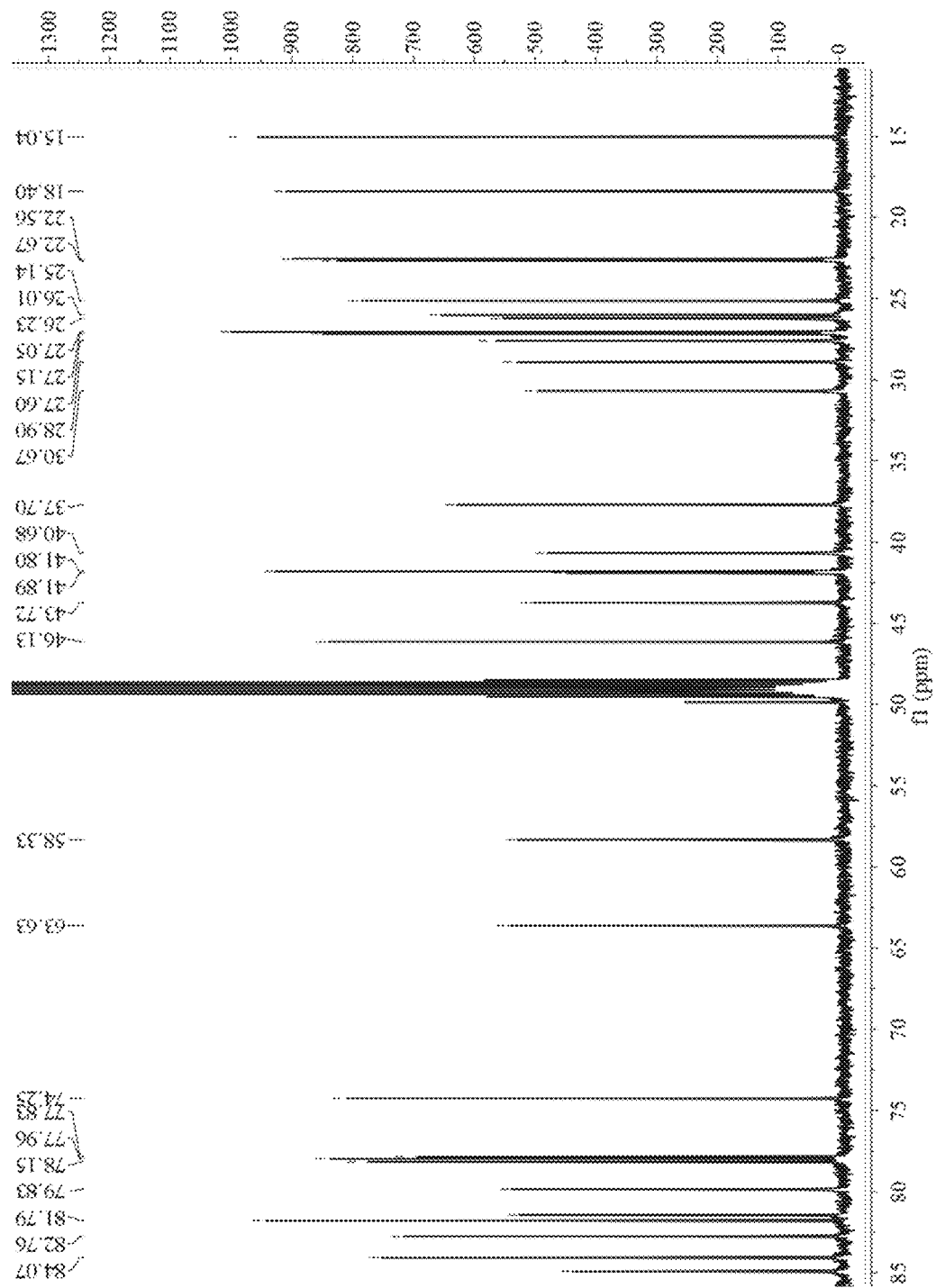
FIG. 8 shows a partial enlarged view of FIG. 7.

The specific information of the compound is as follows:

① the compound is named "KUOYUSU" in Chinese and limaxol A in English;

② chiral C configurations of the compound comprises: C3, R; C6, S; C7, S; C10, S; C11, R; C12, R; C13, R; C14, R; C15, S; C18, S; C19, S; and C22, R with crystal structures shown in FIGS. 1 and 2;

③ physical and chemical properties and spectra data comprise:

① molecular formula: $C_{30}H_{52}O_7$; molecular weight 524;

② state: white needle (column)-like crystals (crystallization solvent: methanol), the crystallization diagrams shown in FIGS. 3 and 4;

③ melting point: 248 to 249° C.;

④ solubility: white needle (column) crystal, insoluble in water, insoluble in acid and alkali, easily soluble in methanol, acetone, soluble in ethanol, ethyl acetate, trichloromethane (hot), and slightly soluble in trichloromethane (cold);

⑤ carbon (C) and hydrogen (H) NMR spectra data, as shown in Table 1; and carbon (C) hydrogen (H) NMR spectra, as shown in FIGS. 5-8; and

TABLE 1

| $^{13}$C and $^1$H-NMR data (500 MHz, in CD$_3$OD) | | |
|---|---|---|
| NO | $\delta_C$ | $\delta_H$ (J in Hz) |
| 1 | | |
| 2 | 78.15 | |
| 3 | 79.83 | 3.61 (d, J = 9.8 Hz, 1H) |
| 4 | 37.70 | 2.10 (m, 1H), 1.67 (m, 1H) |
| 5 | 41.89 | 1.99 (m, 1H), 1.60 (m, 1H) |
| 6 | 41.80 | |
| 7 | 77.83 | 3.26 (dd, J = 11.7, 4.9 Hz, 1H) |
| 8 | 28.90 | 1.69 (m, 1H), 1.46 (m, 1H) |
| 9 | 40.68 | 1.94 (m, 1H), 1.33 (m, 1H) |
| 10 | 46.13 | |
| 11 | 63.63 | 1.01 (d, J = 10.9 Hz, 1H) |
| 12 | 81.46 | 4.04 (dd, J = 10.9, 2.4 Hz, 1H) |
| 13 | 84.91 | 4.29 (dd, J = 7.3, 2.4 Hz, 1H) |
| 14 | 58.33 | 1.42 (d, J = 7.3 Hz, 1H) |
| 15 | 77.96 | |
| 16 | 27.60 | 1.92 (m, 1H), 1.53 (m, 1H) |
| 17 | 43.72 | 1.91 (m, 1H), 1.26 (m, 1H) |
| 18 | 82.76 | 3.28 (ddd, J = 10.9, 4.2, 0.5 Hz, 1H) |
| 19 | 81.79 | |
| 20 | 26.01 | 2.16 (m, 1H), 1.84 (m, 1H) |
| 21 | 30.67 | 2.06 (m, 1H), 1.39 (m, 1H) |
| 22 | 84.07 | 3.86 (d, J = 7.0 Hz, 1H) |
| 23 | 74.25 | |
| 24 | | |
| 25 | 22.56 | 1.06 (m, 3H) |
| 26 | 25.14 | 1.24 (m, 3H) |
| 27 | 15.04 | 0.97 (m, 3H) |
| 28 | 18.40 | 1.29 (m, 3H) |
| 29 | 26.23 | 1.23 (m, 3H) |
| 30 | 22.67 | 1.25 (m, 3H) |
| 31 | 27.15 | 1.42 (m, 3H) |
| 32 | 27.05 | 1.07 (m, 3H) |

Figure 9:
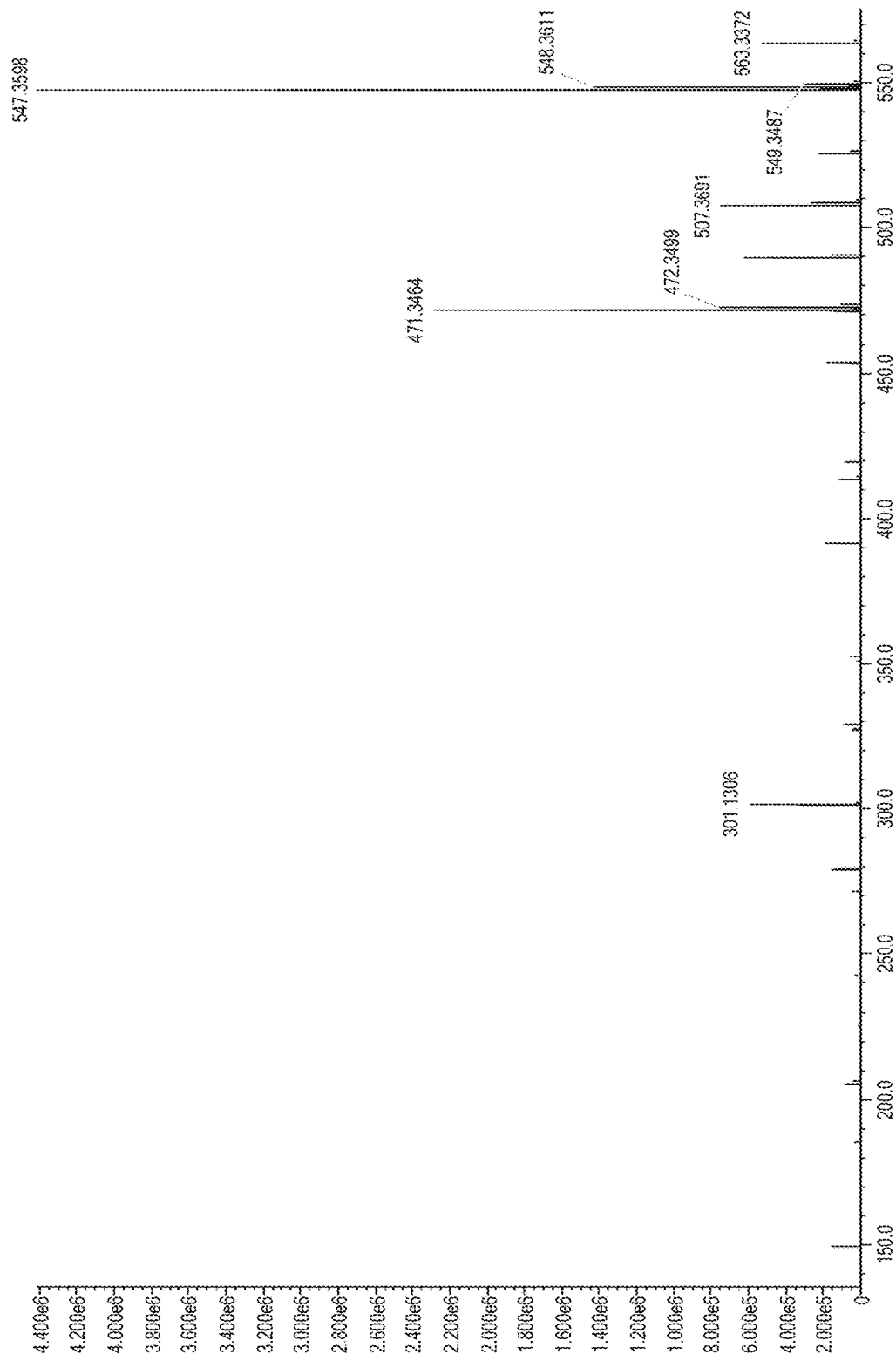
FIG. 9 is mass spectrometry (MS) data chart ([M+Na]+) of the compound of the present application.

⑥ Mass spectrum (MS) data chart, as shown in FIG. 9.

II A Method for Preparing a Compound

Example 2

A method for preparing a compound includes the following steps:

S1: 60 Kg of Limax, after sorting and removing impurities, were pulverized into 20 mesh coarse powder for later use;

S2: into a supercritical CO$_2$ extractor, the Limax coarse powder was added for extraction to obtain an extract under the extraction conditions: pressure: 25 KPa, temperature: 65° C., flow: 400 PV, and extraction time: 4 h.

S3: Into a reactor, the extract, potassium hydroxide and water were added in a weight ratio of "extract:potassium hydroxide:water=1:1:1.5", and mixed evenly; the mixture was heated to 85° C. for a saponification reaction, and the reaction was carried out under stirring for 2 h to obtain saponification reaction liquid A;

S4: the reaction solution A was added into ethyl ether for extraction to separate an ethyl ether layer, followed by washing with water until the water washed solution became neutral, the ethyl ether layer was separated; and the ethyl ether was recovered under reduced pressure to obtain a thick paste A;

S5: thick paste A was added with methanol, dissolved by heating, and filtered; a filtrate was stood to precipitate crystals, and a mother liquor was reserved for later use;

S6: the crystals were subjected to preparative medium pressure liquid phase separation to obtain the compound, the liquid phase conditions being: reversed-phase C18 column, solvent system: methanol:acetonitrile:isopropanol:water (70:20:6:4), and flow rate: 50 ml/min; and S7: the mother liquor of S5 was added with deionized water according to methanol:water (8:2), and heated to reflux to separate a black oil; the methanol solution was filtered out, and the methanol was recovered, and dried; the residue was added with trichloromethane, heated to dissolve, cooled and stood to precipitate crystals, which was filtered to obtain crystals; the crystals were washed with a small amount of trichloromethane, dried, added with methanol, heated to dissolve, cooled, and stood to precipitate crystals; which was filtered, and dried to obtain the compound.

Example 3

A method for preparing a compound includes the following steps:

T1: 100 Kg of Limax, after sorting and removing impurities, were pulverized into 20 mesh coarse powder for later use;

T2: into a multifunctional extraction tank, the coarse Limax powder was put, the solvent n-hexane was added to reflux and extract twice, and filtered; the extract solutions were combined, and the n-hexane was recovered under reduced pressure to obtain thick paste B;

T3: into a reactor, the thick paste B, potassium hydroxide and water were added in a weight ratio of "extract:potassium hydroxide:water=1:1:1.5", and mixed evenly; the mixture was heated to 95° C. for a saponification reaction, and the reaction was carried out under stirring for 3.5 h to obtain saponification reaction liquid B;

T4: the reaction solution B was added to ethyl acetate for extraction to separate the ethyl acetate solution, followed by washing with deionized water until the water washed solution became neutral, the ethyl acetate solution was separated, and the ethyl acetate was recovered under reduced pressure to obtain a thick paste C;

T5: the thick paste C was added with methanol, heated to dissolve, and filtered; the filtrate was left to cool, and stood to precipitate crystals; and a mother liquor was reserved for later use; and T6: the crystals were subjected to preparative medium pressure liquid phase separation to obtain the compound, the liquid phase conditions being: reversed-phase C18 column, solvent system: methanol:acetonitrile:isopropanol:water (70:20:6:4), and flow rate: 50 ml/min; and T7: the mother liquor of T5 was added with deionized water according to methanol:water (8:2), and heated to reflux to separate a black oil; the methanol solution was filtered out, and the methanol was recovered, and dried; the residue was added with trichloromethane, heated to dissolve, cooled and stood to precipitate crystals, which was filtered to obtain crystals; the crystals were washed with a small amount of trichloromethane, dried, added with methanol, heated to dissolve, cooled, and stood to precipitate crystals; which was filtered, and dried to obtain the compound.

Example 4

A method for preparing a compound includes the following steps:

T1: 150 Kg of Limax, after sorting and removing impurities, were pulverized into 20 mesh coarse powder for later use;

T2: into the multifunctional extraction tank, the coarse Limax powder was put, a mixed solvent (trichloromethane:acetone=1:1) was added to reflux and extract twice, and filtered; the extract solutions were combined, and the solvent was recovered under reduced pressure to obtain thick paste B;

T3: into a reactor, the thick paste B, potassium hydroxide and water were added in a weight ratio of "extract:potassium hydroxide:water=1:1:1.5", and mixed evenly; the mixture was heated to 100° C. for a saponification reaction, and the reaction was carried out under stirring for 4 h to obtain saponification reaction liquid B;

T4: the reaction solution B was added to n-butanol for extraction to separate the n-butanol solution, followed by washing with deionized water until the water washed solution became neutral, the n-butanol solution was separated, and the n-butanol was recovered under reduced pressure to obtain a thick paste C;

T5: the thick paste C was added with methanol, heated to dissolve, and filtered; the filtrate was left to cool, and stood to precipitate crystals; and a mother liquor was reserved for later use;

T6: the crystals were taken to prepare the compound through preparative medium-pressure liquid phase separation; the liquid phase condition being: reversed-phase C18 column, solvent system: methanol:acetonitrile:isopropanol:water (70:20:6:4), and flow rate: 50 ml/min;

T7: the mother liquor of T5 was added with deionized water according to methanol:water (8:2), and heated to reflux to separate a black oil; the methanol solution was filtered out, and the methanol was recovered, and dried; the residue was added with trichloromethane, heated to dissolve, cooled and stood to precipitate crystals, which was filtered to obtain crystals; the crystals were washed with a small amount of trichloromethane, dried, added with methanol, heated to dissolve, cooled, and stood to precipitate crystals; which was filtered, and dried to obtain the compound.

Example 5

A method for preparing a compound includes the following steps:

T1: 100 Kg of Limax, after sorting and removing impurities, were pulverized into 20 mesh coarse powder for later use;

T2: into a multifunctional extraction tank, the coarse Limax powder was put, methanol was added to reflux and extract twice, and filtered; the extract solutions were combined, and the methanol was recovered under reduced pressure to obtain thick paste B;

T3: into a reactor, the thick paste B, potassium hydroxide and water were added in a weight ratio of "extract:potassium hydroxide:water=1:1:1.5", and mixed evenly; the mixture was heated to 90° C. for a saponification reaction, and the reaction was carried out under stirring for 3 h to obtain saponification reaction liquid B;

T4: the reaction solution B was added to a mixed solvent (ethyl acetate:ether=1:1) for extraction to separate a mixed solvent layer, combined, followed by washing with deionized water until the water washed solution became neutral, the mixed solvent was separated, and the solvent was recovered under reduced pressure to obtain a thick paste C;

T5: the thick paste C was added with methanol, heated to dissolve, and filtered; the filtrate was left to cool, and stood to precipitate crystals; and a mother liquor was reserved for later use;

T6: the crystals were taken to prepare the compound through preparative medium-pressure liquid phase separation; the liquid phase condition being: reversed-phase C18 column, solvent system: methanol:acetonitrile:isopropanol:water (70:20:6:4), and flow rate: 50 ml/min;

T7: the mother liquor of T5 was added with deionized water according to methanol:water (8:2), and heated to reflux to separate a black oil; the methanol solution was filtered out, and the methanol was recovered, and dried; the residue was added with trichloromethane, heated to dissolve, cooled and stood to precipitate crystals, which was filtered to obtain crystals; the crystals were washed with a small amount of trichloromethane, dried, added with methanol, heated to dissolve, cooled, and stood to precipitate crystals; which was filtered, and dried to obtain the compound.

Example 6

A method for preparing a compound includes the following steps:

S1: 100 Kg of Limax, after sorting and removing impurities, were pulverized into 20 mesh coarse powder for later use;

S2: into a supercritical $CO_2$ extractor, the Limax coarse powder was added for extraction to obtain an extract under the extraction conditions: pressure: 25 KPa, temperature: 65° C., flow: 500 PV, and extraction time: 4 h.

S3: Into a reactor, the extract, potassium hydroxide and water were added in a weight ratio of "extract:potassium hydroxide:water=1:1:1.5", and mixed evenly; the mixture was heated to 100° C. for a saponification reaction, and the reaction was carried out under stirring for 4 h to obtain saponification reaction liquid A;

S4: the reaction solution A was added into ethyl acetate for extraction to separate an ethyl acetate layer, followed by washing with water until the water washed solution became neutral, the ethyl acetate layer was separated; and the ethyl acetate was recovered under reduced pressure to obtain a thick paste A;

S5: thick paste A was added with methanol, dissolved by heating, and filtered; a filtrate was stood to precipitate crystals, and a mother liquor was reserved for later use;

S6: the crystals were subjected to preparative medium pressure liquid phase separation to obtain the compound, the liquid phase conditions being: reversed-phase C18 column, solvent system: methanol:acetonitrile:isopropanol:water (70:20:6:4), and flow rate: 50 ml/min; and S7: the mother liquor of S5 was added with deionized water according to methanol:water (8:2), and heated to reflux to separate a black oil; the methanol solution was filtered out, and the methanol was recovered, and dried; the residue was added with trichloromethane, heated to dissolve, cooled and stood to precipitate crystals, which was filtered to obtain crystals; the crystals were washed with a small amount of trichloromethane, dried, added with methanol, heated to dissolve, cooled, and stood to precipitate crystals; which was filtered, and dried to obtain the compound.

Experimental Study on Pharmacodynamics of the Compound in Drug Withdrawal

I. Study on Therapeutic Effect of the Compound on Withdrawal Symptoms in Morphine-Dependent Rats The inhibitory effect of the compound on morphine withdrawal symptoms in animals was evaluated by replicating a model of induced withdrawal for morphine-dependent rats. The results showed that two doses (0.3, 0.6 g/kg) ig of administration of the compound could partially control the withdrawal symptoms, but had no significant effect on changes of the body weight of rats. The experimental results showed that the compound has a certain detoxification treatment effect on withdrawal symptoms of morphine-dependent rats.

Object of Experiment

It's an object of the experiment to provide a theoretical and pharmacological basis for the further application of the compound in clinic by establishing an animal model of induced withdrawal for morphine-dependent rats to observe the therapeutic effect of the compound on the induced withdrawal symptoms of morphine-dependent rats.

Pharmaceutical Products for Experiment

The compound, provided by Guangxi Jiufu Biotechnology Co., Ltd., batch number: 20160518. Morphine hydrochloride (medicinal powder), provided by a medicinal material supply station of the General Logistics Department of the PLA, batch number: 710303. Naloxone hydrochloride, produced by Sigma, USA, batch number: 111K1379. Sodium chloride injection (normal saline), 500 ml/bottle, produced by Shandong Qidu Pharmaceutical Co., Ltd., batch number: d05100305. Methadone hydrochloride (raw material powder), provided by Tianjin Central Pharmaceutical Co., Ltd., batch number: 020111.

Laboratory Animals for Experiment

Sprague-Dawley (SD) rats, SPF grade, male, 8-week-old, weighing 180-220 g, were provided by the Laboratory Animal Center of Southern Medical University, animal qualification number: SCXK YUE 2011-0015.

After the rats were purchased by the laboratory, they were housed 5 per cage. Cages and trays for rats were cleaned and disinfected before use. The rats had their freedom to drink and eat, and the feed for them was granules produced by the Laboratory Animal Center of Southern Medical University. The rats were kept under the following conditions: temperature 24±2° C., humidity (60±5)%, illumination period 12 h:12 h. Feces and urine trays for the rats were washed once a day, and their drinking bottles were replaced and washed once a day. The breeding room was disinfected regularly and managed by a special person.

Methodology

1. Establishment of a Model of Morphine-Dependent Rats

Fifty SD rats, half males and half females, were randomly divided into 5 groups. Group ① was a blank control group, injected subcutaneously with (sc) normal saline, and groups ②-⑤ were used to replicate the model of morphine-dependent rats according to the dose increasing method, injected subcutaneously with (sc) morphine hydrochloride once every 12 hours (8:00 am, 8:00 pm), with the dose increased from 5 mg/kg each time to 80 mg/kg each time, and this proceeded until the $7^{th}$ day at which time the injection amount was 0.2 ml/100 g, the administration volume being the same for each group.

2. Therapeutic Effect of the Pharmaceutical Products on Induced Withdrawal Symptoms of Morphine-Dependent Rats On the $8^{th}$ day of the experiment, morphine administration was stopped and a naloxone-induced withdrawal test was performed. The groups were given different treatments: the blank control group ① was given normal saline (ig) of a volume; the morphine model group ② was given normal saline (ig) of the same volume; the positive control group ③ was given 20 mg/kg (ig) methadone; groups ④ and ⑤ were groups of the compound at low and high doses which were 0.3 g/kg and 0.6 g/kg, respectively, and the compound (ig) was administered at the above doses. The administration continued for 3 days for each group of rats. Rats were free to drink and eat. Naloxone (5.0 mg/kg, ip) was given 45 min after administrations on d1 and d3 during the treatment to induce withdrawal symptoms, and withdrawal reaction in 30 min and body weights one hour before and after the inducement were observed.

The evaluation criteria of withdrawal symptoms of rats were established by referring to the Tomoji Yanagita evaluation criteria and our pre-experimental results (see Appendix Table 2). Times of shaking like a wet dog, stereotyped acts, erecting and jumping in 30 minutes were directly scored; symptoms such as ptosis, irritability, tooth tremor, chewing, pilus erection, abnormal posture and rapid respiration were scored every 5 minutes; symptoms such as diarrhea, lacrimation, salivation and rhinorrhea were scored every 30 minutes. The sum of all scores was the total score of the withdrawal reaction. See Appendix Table 2.

3. Statistical Processing

The experimental data were expressed as x±s. The statistical software SPSS 13.5 was used to carry out one-way ANOVA (analysis of variance) or two-independent-sample t-test of completely random design data. An LSD method was used when the variance of multiple comparisons between groups was uniform, and a Games-Howell method was used when the variance was not uniform. $P<0.05$ showed that the difference has statistical meaning.

Results

1. Effect of the Pharmaceutical Products on Induced Withdrawal Symptoms of Morphine-Dependent Rats No significant withdrawal symptoms were observed in the blank control group after naloxone administration. Rats of the morphine-dependent model group showed significant withdrawal symptoms 1 and 3 days after withdrawal induced by naloxone, which was significantly different from the blank control group ($P<0.01$). Morphine-dependent rats, after being treated with the compound, had their scores of withdrawal symptoms decreased in different degrees. The scores of withdrawal symptoms of the low and high dose groups were significantly different from those of the morphine model group ($P<0.05$ or $P<0.01$). See Table 3.

TABLE 3

Scores of Induced Withdrawal Symptoms of Morphine-Dependent Rats (x ± s, n = 10)

| Groups | Scores of induced withdrawal symptoms of rats | |
|---|---|---|
| | d1 | d3 |
| Blank control group | 4.5 ± 3.88 | 1.4 ± 1.69 |
| Morphine model group | 81.3 ± 32.11** | 44.5 ± 8.09** |
| Group at low dose of the compound | 74.9 ± 42.03** | 25.5 ± 12.26**# |
| Group at high dose of the compound | 53.8 ± 16.23**# | 22.1 ± 10.90**# |
| Positive control group | 49.35 ± 14.41**## | 35.6 ± 18.73** |

*$P < 0.05$,
**$P < 0.01$, in comparison with the blank control group.
$P < 0.05$,
$P < 0.01$, in comparison with the morphine model group.

2. Effect of the Pharmaceutical Products on Induced Withdrawal Weight Changes of Morphine-Dependent Rats The results showed that there were no significant changes in body weight after naloxone administration on the $8^{th}$ and $10^{th}$ days of the experiment (d1 and d3 during the withdrawal) for the blank control group which was not given morphine. After naloxone inducement, the body weight of the morphine-dependent rats decreased significantly along with arising withdrawal symptoms, on d1 and d3 during the withdrawal, the body weight changes of rats of the morphine model group were significantly different from those of the blank control group, $P<0.01$; the body weight changes of the low and high dose groups and the positive control group were significantly different from those of the blank control group, $P<0.01$; the body weight changes of the high dose group and the positive control group were significantly different from the morphine model group on d1 during the withdrawal, $P<0.05$. There were no significant body weight changes after naloxone inducement on d3 during the withdrawal for rats of the morphine model group. See Table 4.

TABLE 4

Body Weight Change (Body Weight before Inducement − Body Weight after Inducement) for Each Group of Rats (x ± s, n = 10)

| Groups | d1 (g) | d3 (g) |
|---|---|---|
| Blank control group | 0.5 ± 3.20 | 1.0 ± 1.05 |
| Morphine model group | 10.5 ± 5.48** | 3.6 ± 2.41** |
| Group at low dose of the compound | 11.8 ± 3.25** | 4.5 ± 2.59** |
| Group at high dose of the compound | 14.7 ± 4.08**# | 1.9 ± 2.13** |
| Positive control group | 15.6 ± 6.39**# | 2.6 ± 2.75** |

*$P < 0.05$,
**$P < 0.01$, in comparison with the blank control group.
$P < 0.05$,
$P < 0.01$, in comparison with the morphine model group.

Conclusion

1. Morphine dependence was observed in SD rats treated with increasing doses of morphine, and significant withdrawal symptoms were observed in SD rats subjected to naloxone inducement. The results showed that the model of induced withdrawal for morphine-dependent rats was successfully replicated.

2. Two doses of the compound (0.3, 0.6 g/kg) ig for 3 days inhibited the induced withdrawal symptoms of morphine-dependent rats, and the score of withdrawal symptoms pf the high dose group was significantly lower than that of the morphine model group. The two groups of low and high doses of the compound had no significant effect on body weight loss in addicted rats.

APPENDIX TABLE 2

Table of Records of Withdrawal Symptoms of Rats

| Countable symptoms | Times of occurrence in 30 minutes | | | | | |
|---|---|---|---|---|---|---|
| shaking like a wet dog | 1 point per time | | | | | |
| Stereotyped acts | 0.5 point per time | | | | | |
| Erecting | 1 point per time | | | | | |
| Jumping | 2 point per time | | | | | |
| Uncountable symptoms | 1-5 min | 6-10 min | 11-15 min | 16-20 min | 21-25 min | 26-30 min |
| Abnormal posture (2) | | | | | | |
| Pilus erection (1) | | | | | | |
| Tooth tremor (2) | | | | | | |
| Rapid respiration (3) | | | | | | |
| Ptosis (2) | | | | | | |
| Irritability (2) | | | | | | |
| Diarrhoea | Soft feces (4), shapeless feces (8), none (0) | | | | | |
| Lacrimation | Slight (1), obvious (2), none (0) | | | | | |
| Rhinorrhea | Slight (1), obvious (2), none (0) | | | | | |
| Salivation | Slight (2), obvious (3), none (0) | | | | | |

II. Study on Therapeutic Effect of the Compound on Induced Withdrawal Symptoms of Morphine-Dependent Mice The animal model of induced withdrawal of morphine-dependent mice was established by subcutaneous injection of increasing doses of pharmaceutical products. The results showed that: the administration (ig) of the compound had therapeutic effects on induced withdrawal symptoms of the morphine-dependent mice, inhibited jumping reaction during the induced withdrawal of the morphine-dependent mice, and inhibited weight loss of the morphine-dependent mice. The effect of the low dose group was better than that of the high dose group, which suggested that the compound was a potential pharmaceutical product for drug Withdrawal.

Object of Experiment

It's an object of the experiment to provide a pharmacological basis for development and application of the compound by establishing a model of induced withdrawal of morphine-dependent mice to observe the therapeutic effect of the compound on induced withdrawal symptoms of the morphine-dependent mice.

Pharmaceutical Products for Experiment

The compound, provided by Guangxi Jiufu Biotechnology Co., Ltd., batch number: 20160518. Morphine hydrochloride (medicinal powder), provided by a medicinal material supply station of the General Logistics Department of the PLA, batch number: 710303. Naloxone hydrochloride, produced by Sigma, USA, batch number: 111K1379. Sodium chloride injection (normal saline), 500 ml/bottle, produced by Shandong Qidu Pharmaceutical Co., Ltd., batch number: d05100305. Methadone hydrochloride (raw material powder), provided by Tianjin Central Pharmaceutical Co., Ltd., batch number: 020111.

The compound was dissolved to the desired concentration by heating with vegetable oil and prepared prior to the experiment.

Laboratory Animals for Experiment

Kunming mice, half males and half females, weighing 20-24 g, were provided by the Laboratory Animal Center of Southern Medical University. Grade SPF, animal qualification number: SCXK YUE 2011-0015.

The mice were divided into males and females, housed 5 per cage. Cages and trays for the mice were cleaned and disinfected before use. The mice had their freedom to drink and eat, and the feed for them was granules produced by the Laboratory Animal Center of Southern Medical University. The mice were kept under the following conditions: temperature 24±2° C., humidity (60±5)%, illumination period 12 h:12 h. Padding for the rats was replaced once a week, and their drinking bottles were replaced and washed once a day. The breeding room was disinfected regularly and managed by a special person.

Test Control

Blank control group: administered (ig) with equal volume of vegetable oil.

Positive control group: methadone hydrochloride. Positive control mice were administered 20 mg/kg/day (ig).

Methodology

1. Establishment of the Model of Induced Withdrawal of the Morphine-Dependent Mice The model of morphine-dependent mice was replicated by the dose-increasing method. Fifty Kunming mice, half males and half females, were randomly divided into 5 groups. Group ① was a blank control group, injected subcutaneously (sc) with normal saline (0.2 ml/10 g), and groups ②-⑤ were used to replicate the model of morphine-dependent mice by the dose-increasing method. Morphine was administered (sc) twice daily (8:00, 20:00) in a volume of 0.1 ml/10 g, with the dose increased from 25 mg/kg day by day to 160 mg/kg on the $6^{th}$ day, as such the model of morphine-dependent mice was established, the dosing volumes being the same for each group.

2. Therapeutic Effect of the Pharmaceutical Products on Induced Withdrawal Symptoms of the Morphine-Dependent Mice On the $7^{th}$ day of the experiment, morphine administration was stopped and a naloxone-induced withdrawal test was performed. The groups were given different treatments: the blank control group ① was given vegetable oil (ig) of a volume; the morphine model group ② was given vegetable oil (ig) of the same volume; the positive control group ③ was given 20 mg/kg (ig) methadone; groups ④ and ⑤ were groups of the compound at low and high doses which were 0.4 g/kg and 0.8 g/kg, respectively, and the compound (ig) was administered at the above doses. The administration continued for 3 days for each group. Mice were free to drink and eat. Naloxone (8.0 mg/kg, ip) was given 1 h after administrations on d1 and d3 during the treatment to induce withdrawal symptoms, and jumping reaction in 30 min and body weights before and after the inducement were observed.

3. Statistical Processing

The experimental data were expressed as x±s. The statistical software SPSS 13.5 was used to carry out one-way ANOVA (analysis of variance) or two-independent-sample t-test of completely random design data. An LSD method was used when the variance of multiple comparisons between groups was uniform, and a Games-Howell method was used when the variance was not uniform. P<0.05 showed that the difference has statistical meaning. The counting data were checked with $\chi^2$.

Results

1. Effect of the Pharmaceutical Products on Jumping Reaction of the Mice

After 7 days of continuous morphine administration (sc), all the morphine-dependent mice showed a significant jump reaction after being induced by naloxone. In the blank control group without morphine given, the mice had no obvious withdrawal symptoms after naloxone administration (ip), and only a few mice had one or two times of jump reaction. After the administration of the compound (ig), the number and times of jumping reaction of the mice in the low and high dose groups were reduced. Compared with morphine model group, the number and times of jumping reaction of the mice in the low and high dose groups and the positive control group were significantly reduced, P<0.01. Compared with the high dose group, the low dose group had significant difference, P>0.05. See Table 5 and Table 6.

TABLE 5

Times of Induced Withdrawal Jumping Reactions of the Morphine-Dependent Mice (x ± s, n = 10)

| Groups | Times of jumping reactions of mice (per 30 min) | |
|---|---|---|
| | d1 | d3 |
| Blank control group | 0.4 ± 0.699 | 0.5 ± 0.84 |
| Morphine model group | 63.2 ± 14.65** | 12.5 ± 6.09** |
| Low dose group | 13.5 ± 10.29**## | 6.2 ± 5.86*# |
| High dose group | 35.0 ± 12.28**## | 8.5 ± 2.68**## |
| Positive control group | 25.1 ± 6.90**## | 22.9 ± 6.81**## |

*P < 0.05,
**P < 0.01, in comparison with the blank control group.
P < 0.05,
P < 0.01, in comparison with the morphine model group.

TABLE 6

Number of Induced Withdrawal Jumping Reactions of the Morphine-Dependent Mice (n = 10)

| Groups | Numbers of jumping reactions of mice | | | |
|---|---|---|---|---|
| | d1 | percentage (%) | d3 | percentage (%) |
| Blank control group | 3 | 30% | 3 | 30% |
| Morphine model group | 10 | 100% | 10 | 100% |
| Low dose group | 10 | 100% | 10 | 100% |
| High dose group | 10 | 100% | 10 | 100% |
| Positive control group | 10 | 100% | 10 | 100% |

2. Effect of the Pharmaceutical Products on Body Weight of the Mice

As can be seen from Table 7, the body weight of the morphine-dependent mice decreased significantly along with the withdrawal symptoms after naloxone inducement and increased after treatment with the compound. On d1 during the withdrawal, the body weight changes of the low and high dose groups were significantly different from those of the morphine model group, P<0.05 or P<0.01. Compared with morphine model group, the body weight of mice in the positive control group was significantly different, P<0.01). On the 3rd day during the withdrawal, there was no significant difference in body weight among the groups.

TABLE 7

Weight Change Results (x ± s, n = 10) for Each Group of Mice. Body weights of mice before and after induced withdrawal (g)

| Groups | d1 | d3 |
|---|---|---|
| Blank control group | 0.19 ± 0.17 | 0.34 ± 0.31 |
| Morphine model group | 0.53 ± 0.19** | 0.55 ± 0.29 |
| Low dose group | 0.18 ± 0.13## | 0.36 ± 0.28 |

TABLE 7-continued

Weight Change Results (x ± s, n = 10) for Each Group of Mice. Body weights of mice before and after induced withdrawal (g)

| Groups | d1 | d3 |
|---|---|---|
| High dose group | 0.26 ± 0.21# | 0.43 ± 0.23 |
| Positive control group | 0.22 ± 0.19## | 0.46 ± 0.23 |

* P < 0.05,
**P < 0.01, in comparison with the blank control group.
P < 0.05,
P < 0.01, in comparison with the morphine model group.

Conclusion

The administration of the compound (ig) had a therapeutic effect on induced withdrawal symptoms of the morphine-dependent mice, inhibited the induced withdrawal jumping reaction of the morphine-dependent mice, and promoted recovery of the weight loss of the morphine-dependent mice. Within the dose range used in this experiment, the effect of the low dose group had a more significant effect than that of the high dose group.

III. Study on Effect of the Compound on Conditioned Place Preference of Morphine-Induced Mice The effect of the compound on morphine-induced psychological dependence of animals was evaluated by establishing a model of conditioned place preference of morphine-dependent mice. The results showed that administration of two doses (0.4, 0.8 g/kg) of the compound (ig) for 3 days had no significant effect on conditioned place preference of the morphine-induced mice.

Object of Experiment

It's an object of the experiment provide a pharmacological experimental basis for clinical application of the compound by a model of morphine-induced psychological dependence of mice to evaluate the effect of the compound on the morphine-induced psychological dependence.

Pharmaceutical Products for Experiment

The compound, provided by Guangxi Jiufu Biotechnology Co., Ltd., batch number: 20160518. Morphine hydrochloride (medicinal powder), provided by a medicinal material supply station of the General Logistics Department of the PLA, batch number: 710303. Sodium chloride injection (normal saline), 500 ml/bottle, produced by Shandong Qidu Pharmaceutical Co., Ltd., batch number: d05100305. Methadone hydrochloride (raw material powder), provided by Tianjin Central Pharmaceutical Co., Ltd., batch number: 020111.

Laboratory Animals for Experiment

Kunming mice, half males and half females, weighing 20-24 g, were provided by the Laboratory Animal Center of Southern Medical University. Grade SPF, animal qualification number: SCXK YUE 2011-0015.

The mice were divided into males and females, housed 5 per cage. Cages and trays for the mice were cleaned and disinfected before use. The mice had their freedom to drink and eat, and the feed for them was granules produced by the Laboratory Animal Center of Southern Medical University. The mice were kept under the following conditions: temperature 24±2° C., humidity (60±5)%, illumination period 12 h:12 h. Padding for the rats was replaced once a week, and their drinking bottles were replaced and washed once a day. The breeding room was disinfected regularly and managed by a special person.

Instrument for Experiment

A conditioned place preference box was made according to the literature, the box body was composed of black and white cuboids (15 cm×15 cm×15 cm), a movable partition plate is arranged in the middle of the box body, and the mice can freely move from one cuboid to another when the partition plate is removed. Inner surfaces of one cuboid of the box body except the glass panel is painted black, the bottom plate is made to be a rough surface by using a soft blanket, the other cuboid of the box body except the glass surface is painted white, the bottom plate is made to be a smooth surface, and the whole experimental box has visual and tactile cues.

Methodology

1. Determination of Base Line

The mice were acclimatized for 3 days, the natural place preference time of the mice was measured before the administration, so that the mice with obvious preference on one cuboid of the experimental box were excluded to clear the effect of unconditional place preference on the results. During measurement, the partition plate in the middle of the experimental box was removed, the mice were placed between the two cuboids and observed for 15 minutes one by one, and the duration of each of the mice staying in each cuboid was recorded on the basis of the positions of their heads. The observation was conducted under sound insulation conditions. The results showed that almost all mice prefer the black cuboid. Thus, the white cuboid was used as the non-preferred side (i.e., the companion box).

2. Training and Determination of Morphine-Induced Place Preference Effect

Fifty KM mice, half males and half females, qualified after the base line determination, were randomly divided into 5 groups (n=10): a blank control group, a morphine model group (9 mg/kg), a methadone group (methadone 20 mg/kg+morphine 9 mg/kg), a low dose Compound group (the extract 0.4 g/kg+morphine 9 mg/kg) and a high dose Compound group (the extract 0.8 g/kg+morphine 9 mg/kg). The mice in the other groups were given morphine (9 mg/kg, sc) every morning (9:00) and normal saline (10 ml/kg, sc) every afternoon (17:00), at an interval of 8 hours, except that normal saline was provided for the blank control group in both the morning and afternoon. After morphine injection in the morning, the mice were immediately placed in the white cuboid which was the non-preferred side, and after saline injection in the afternoon, the mice were immediately placed in the black cuboid which was the preferred side, leaving either of them there for 45 min. After 6 consecutive days of training and administration, the mice developed conditioned place preference. The place preference test was performed 24 h after the last morphine injection. The partition plate of the preferred box was removed, the mice were placed into the box body one by one and observed for 15 minutes, and the duration of each of the mice staying in each cuboid was recorded.

3. Administration of Test Pharmaceutical Products

Starting from the $4^{th}$ day of morphine administration, each group was given the corresponding pharmaceutical product 45 min before morphine administration, the compound and methadone were given intragastrically, and the blank control group and morphine model group were given the same volume of normal saline ig. Each group was administered for 3 consecutive days.

4. Statistical Processing

The experimental data were expressed as x±s. The statistical software SPSS 13.5 was used to carry out one-way ANOVA (analysis of variance) or two-independent-sample t-test of completely random design data. An LSD method was used when the variance of multiple comparisons between groups was uniform, and a Games-Howell method was used when the variance was not uniform. $P<0.05$ showed that the difference has statistical meaning.

Results

There was no significant difference seen from the duration of the mice staying in the white cuboid for the control group after administration, $P>0.05$. Compared with the blank control group and the situation before administration, the duration of the mice in the white cuboid was significantly prolonged for the morphine model group, $P<0.01$, indicating that the mice developed significant place preference. After each group being administered for 3 consecutive days, there was no significant difference in the duration of the mice staying in the white box for the low dose group (0.4 g/kg) and the high dose group (0.8 g/kg) compared with the morphine model group, $P>0.05$, but compared with the situation before administration, the duration of the mice staying in the white cuboid was prolonged for the two groups, $P<0.05$. See Table 8.

TABLE 8

Effect of Pharmaceutical Products on the Development of Morphine-Induced Place Preference of mice (x ± s, n = 10)

| Groups | Duration of mice staying in companion box (s) | |
|---|---|---|
| | Before administration | After administration |
| Blank control group | 366.5 ± 93.19 | 360.9 ± 75.54 |
| Morphine model group | 282.5 ± 90.69 | 578.6 ± 136.83**ΔΔ |
| Methadone group | 333.7 ± 114.95 | 499.6 ± 123.26*ΔΔ |
| Low dose Compound group | 296.0 ± 142.93 | 438.1 ± 116.45#Δ |
| High dose Compound group | 256.3 ± 114.43* | 511.8 ± 90.66*ΔΔ |

*P < 0.05,
**P < 0.01, in comparison with the blank control group.
P < 0.05,
P < 0.01, in comparison with the morphine model group;
ΔP < 0.05,
ΔΔP < 0.01, in comparison with the situation before administration.

Conclusion

The conditioned place preference test is a new method developed abroad in the 1980s to evaluate neuropsychiatric dependence potential. The method has the advantages of short period, simple equipment, low cost and the like. In this experiment, a morphine-induced place preference model was established to evaluate the effect of the compound on morphine-induced psychological dependence of mice, and the anti-opioid effect of the compound was evaluated scientifically. The results showed that the compound had no significant effect on morphine-induced place preference of mice.

IV. Study on Analgesic Effect of the Compound

The analgesic effect of the compound was studied by acetic acid writhing test and hot plate test. The results showed that the single administration of low and high doses of the compound (0.4, 0.8 g/kg, ig) had no obvious analgesic effect.

Object of Experiment

It's an object of the experiment provide a pharmacological basis for clinical application of the compound by an animal analgesic experiment to observe and evaluate the analgesic effect of Chinese medicine preparations of the compound.

Pharmaceutical Products for Experiment

The compound, provided by Guangxi Jiufu Biotechnology Co., Ltd., batch number: 20160518. Glacial Acetic Acid, Xinning Chemical Plant, Shantou, Guangdong, batch number: 20150514, prepared to be at a concentration of 6% with water for injection, prepared when use. Batch Number: 111K1379. Sodium chloride injection (normal saline), 500 ml/bottle, produced by Shandong Qidu Pharmaceutical Co., Ltd., batch number: d05100305. Methadone hydrochloride (raw material powder), provided by Tianjin Central Pharmaceutical Co., Ltd., batch number: 020111.

The compound was dissolved to the desired concentration by heating with vegetable oil and prepared prior to the experiment.

Laboratory Animals for Experiment

Kunming mice, half males and half females, weighing 20-24 g, were provided by the Laboratory Animal Center of Southern Medical University. Grade SPF, animal qualification number: SCXK YUE 2011-0015.

The mice were divided into males and females, housed 5 per cage. Cages and trays for the mice were cleaned and disinfected before use. The mice had their freedom to drink and eat, and the feed for them was granules produced by the Laboratory Animal Center of Southern Medical University. The mice were kept under the following conditions: temperature 24±2° C., humidity (60±5)%, illumination period 12 h:12 h. Padding for the rats was replaced once a week, and their drinking bottles were replaced and washed once a day. The breeding room was disinfected regularly and managed by a special person.

Instrument for Experiment

Auto-temperature control hot plate, YLS-6A, provided by the Equipment Maintenance and Supply Station of Shandong Academy of Medical Sciences.

Methodology

1. Acetic Acid Writhing Test of Mice

Forty Kunming mice, male, were fasted for 12 h before the experiment but free to drink water. They were randomly divided into 4 groups: a blank control group, a low dose Compound group, a high dose Compound group, and a positive control group. All the mice were fasted for 12 h before the experiment but free to drink water. The mice were administered (ig) at a low dose (0.4 g/kg) and a high dose (0.8 g/kg) of the compound, at a volume of 0.2 ml per 10 g body weight. The positive control group was administered (ip) methadone (20 mg/kg) and the blank control group was given (ig) the same volume of normal saline. Forty-five minutes after administration, each mouse was given (ip) 0.6% acetic acid, 0.2 ml for each. The mice were then observed for writhing reaction, with abdominal contraction and hind limb extension or hip elevation regarded as positive. Times of writhing in 20 min were recorded starting from 5 min after acetic acid injection. The analgesic effect was evaluated by taking completely inhibiting writhing reaction induced by acetic acid as an indicator.

2. Hot Plate Test of Analgesic Effect

Kunming mice, female, were selected. And a selection among them was conducted prior to the test. The hot plate was adjusted to 55° C.±0.5° C., the female mice were placed on the hot plate, and the duration (in seconds) required from placing the mice on the hot plate until the mice licked their feet as the normal pain threshold of the mice. All those who licked their feet within 5 s or after 30 s and jumped were abandoned. Forty qualified mice were selected and randomly divided into 4 groups: a blank control group, a low dose Compound group, a high dose Compound group, and a positive control group, 10 mice per group. The normal pain threshold of each mouse was measured repeatedly, and the average of two measurements was taken as the pre-administration pain threshold of the mouse. Each group was then administered (at doses and by delivery routes as above), 0.2 ml per 10 g body weight. The pain threshold of each group was measured 60 min and 120 min after administration. If a mouse remained unresponsive for more than 60 seconds on the hot plate, its pain threshold was calculated as 60 seconds.

3. Statistical Processing

The experimental data were expressed as x±s. The statistical software SPSS 13.5 was used to carry out one-way ANOVA (analysis of variance) or two-independent-sample t-test of completely random design data. An LSD method was used when the variance of multiple comparisons between groups was uniform, and a Games-Howell method was used when the variance was not uniform. P<0.05 showed that the difference has statistical meaning. The counting data were checked with $\chi^2$.

Results

1. Effect of the Pharmaceutical Products on Acetic Acid Writhing Response of Mice The mice in each group showed writhing reaction after acetic acid administration (ip). There was no significant difference of the low and high dose groups from the blank control group, P>0.01. The number of positive writhing reaction was significantly different from that of the methadone group (positive control group), P<0.0. See Table 9.

TABLE 9

Times of Acetic Acid Writhing for Each Group of Mice (x ± s, n = 10)

| Groups | Delivery route | Times of writhing |
|---|---|---|
| Blank control group | ig | 41.4 ± 23.49 |
| Low dose group | ig | 37.10 ± 15.69[##] |
| High dose group | ig | 39.6 ± 13.21[##] |
| Positive control group | im | 8.7 ± 3.74** |

*P < 0.05,
**P < 0.01, in comparison with the blank control group.
P < 0.01, in comparison with the positive control group.

2. Effect of the Compound on Pain Threshold Induced by Heat of Mice

There was no significant change in pain threshold before and after administration for the blank control group, P>0.05. The pain threshold of the positive group after administration was longer than that before administration, which had a significant meaning, P<0.01. There was no significant difference of pain thresholds, measured at all the moments, of the low and high dose groups from the blank control group or the situation before administration, P>0.05, P<0.01. See Table 10.

TABLE 10

Pain Thresholds Measured by Hot Plate Test for Each Group of Mice (x ± s, n = 10)

| Groups | Pain threshold before administration | Pain thresholds at different moments/s | |
|---|---|---|---|
| | | 60 min | 120 min |
| Blank control group | 24.5 ± 5.18 | 25.2 ± 8.38 | 26.7 ± 9.03 |
| Low dose group | 23.7 ± 4.95 | 25.4 ± 10.10[##] | 29.3 ± 13.41[##] |
| High dose group | 24.3 ± 5.51 | 27.0 ± 11.32[##] | 25.9 ± 12.52[##] |

TABLE 10-continued

Pain Thresholds Measured by Hot Plate Test for Each Group of Mice (x ± s, n = 10)

| Groups | Pain threshold before administration | Pain thresholds at different moments/s | |
|---|---|---|---|
| | | 60 min | 120 min |
| Positive control group | 24.4 ± 5.72 | 58.4 ± 9.05**▲▲ | 51.5 ± 10.11**▲▲ |

*P < 0.05,
**P < 0.01, in comparison with the blank control group.
P < 0.05,
P < 0.01, in comparison with the positive control group.
▲▲P < 0.01, in comparison with the situation before administration.

Conclusion

The results of the acetic acid writhing test and the hot plate test of analgesic effect on mice showed that there was none obvious analgesic effect of the compound (ig) within the dose range used in this experiment.

V. Study on Sedative and Hypnotic Effects of the Compound

In this experiment, the sedative effect of the compound was observed by a spontaneous activity test, a test of inducing mice to sleep by a sub-threshold dose of pentobarbital sodium and a test of sleeping duration of mice. The results showed that low and high doses of the compound (0.4, 0.8 g/kg, ig) could significantly reduce the spontaneous activity of mice, inhibit the increase of excitability induced by morphine and amphetamine, increase the number of mice that fell asleep induced by a sub-threshold dose of pentobarbital sodium, and significantly prolong the sleeping duration induced by pentobarbital sodium. This study showed that the compound had certain sedative and hypnotic effects.

Object of Experiment

It's an object of the experiment provide a therapeutic basis for clinical application of the compound by an animal sedative and hypnotic experiment to observe and evaluate the sedative and hypnotic effects of Chinese medicine preparations of the compound.

Pharmaceutical Products for Experiment

The compound, provided by Guangxi Jiufu Biotechnology Co., Ltd., batch number: 20160518. Morphine hydrochloride (medicinal powder), provided by a medicinal material supply station of the General Logistics Department of the PLA, batch number: 710303. Amphetamine Hydrochloride, provided by National Narcotics Laboratory. Pentobarbital sodium (imported and subpackaged), Sinopharm Chemical Reagent Co., Ltd., batch number: F20120405. Estazolam, produced by Linfen Pharmaceutical Factory, Shanxi, batch number: 120328. Sodium chloride injection (physiological saline), 500 ml/bottle, produced by Shandong Qidu Pharmaceutical Co., Ltd., batch number: D05100305.

The compound was dissolved to the desired concentration by heating with vegetable oil and prepared prior to the experiment.

Laboratory Animals for Experiment

Kunming mice, half males and half females, weighing 20-24 g, were provided by the Laboratory Animal Center of Southern Medical University. Grade SPF, animal qualification number: SCXK YUE 2011-0015.

The mice were divided into males and females, housed 5 per cage. Cages and trays for the mice were cleaned and disinfected before use. The mice had their freedom to drink and eat, and the feed for them was granules produced by the Laboratory Animal Center of Southern Medical University. The mice were kept under the following conditions: temperature 24±2° C., humidity (60±5)%, illumination period 12 h:12 h. Padding for the rats was replaced once a week, and their drinking bottles were replaced and washed once a day. The breeding room was disinfected regularly and managed by a special person.

Instrument for Experiment

YLS-1A multifunctional recorder for spontaneous activities of small animals, produced by the Equipment Station of Shandong Academy of Medical Sciences.

Methodology

1. Mouse Spontaneous Activity Test

Forty Kunming mice, half males and half females, were fasted for 12 h but free to drink water. The mice were randomly divided into four groups: a blank control group, a low does Compound group (0.4 g/kg, ig), a high dose Compound group (0.8 g/kg, ig) and a positive drug control group (Estazolam, 2 mg/kg). The mice were placed into the YLS-1A multifunctional recorder for spontaneous activities of small animals. After 5 minutes of adaptation, the number of the mice's spontaneous activities before administration were recorded, and the recording lasted for 10 minutes. The room was kept quiet during recording, at a room temperature of 20-24° C. After this, each group of mice was administered according to the above doses, and the number of spontaneous activities within 10 min were recorded 45 min later. The blank control group was given the same volume of normal saline (ig).

2. Morphine-Induced Hyperexcitability Test of Mice

Forty Kunming mice, half males and half females, were fasted for 12 h but free to drink water. The mice were randomly divided into four groups: a blank control group, a low does Compound group (0.4 g/kg, ig), a high dose Compound group (0.8 g/kg, ig) and a positive drug control group (Estazolam, 2 mg/kg). The mice were placed into the YLS-1A multifunctional recorder for spontaneous activities of small animals.

After 5 minutes of adaptation, the number of the mice's spontaneous activities before administration were recorded, and the recording lasted for 10 minutes. The room was kept quiet during recording, at a room temperature of 20-24° C. After this, each group of mice was administered according to the above doses, and the blank control group was given the same volume of normal saline (ig). Thirty minutes after administration, each mouse was given an intraperitoneal injection of morphine (10 mg/kg). Fifteen minutes later, the mice were placed in the recorder to observe and record the number of activities within 10 min.

3. Amphetamine-Induced Hyperexcitability Test of Mice

Forty Kunming mice, half males and half females, were fasted for 12 h but free to drink water. The mice were randomly divided into four groups: a blank control group, a low does Compound group (0.4 g/kg, ig), a high dose Compound group (0.8 g/kg, ig) and a positive drug control group (Estazolam, 2 mg/kg). The mice were placed into the YLS-1A multifunctional recorder for spontaneous activities of small animals. After 5 minutes of adaptation, the number of the mice's spontaneous activities before administration were recorded, and the recording lasted for 10 minutes. The room was kept quiet during recording, at a room temperature of 20-24° C. After this, each group of mice was administered according to the above doses, and the blank control group was given the same volume of normal saline (ig). Thirty minutes after administration, each mouse was given an intraperitoneal injection of amphetamine (8 mg/kg). Fifteen minutes later, the mice were placed in the recorder to observe and record the number of activities within 10 min.

4. Test of Inducing the Mice to Sleep by a Subthreshold Dose of Pentobarbital Sodium Eighty Kunming mice, half males and half females, were fasted for 12 h but free to drink water. The mice were randomly divided into four groups: a blank control group, a low does Compound group (0.4 g/kg, ig), a high dose Compound group (0.8 g/kg, ig) and a positive drug control group (Estazolam, 2 mg/kg). each group of mice was administered according to the above doses (ig), and the blank control group was given the same volume of normal saline. Forty-five minutes later, each mouse was given (ip) 30 mg/kg pentobarbital sodium, and the number of mice falling asleep within 15 min was recorded by taking the absence of righting reflex more than 1 min as the indicator of falling asleep.

5. Test of Sleeping Duration Induced by a Threshold Dose of Pentobarbital Sodium Forty Kunming mice, half males and half females, were fasted for 12 h but free to drink water. The mice were randomly divided into four groups: a blank control group, a low does Compound group (0.4 g/kg, ig), a high dose Compound group (0.8 g/kg, ig) and a positive drug control group (Estazolam, 2 mg/kg). each group of mice was administered according to the above doses (ig), and the blank control group was given the same volume of normal saline. Forty-five minutes later, each mouse was given (ip) 50 mg/kg pentobarbital sodium, and then the sleeping duration of each group of mice was recorded (taking the disappear of righting reflex after administration as the indicator of falling asleep, and the recovery of righting reflex as the end time of the sleep).

6. Statistical Processing

The experimental data were expressed as x±s. The statistical software SPSS 13.5 was used to carry out one-way ANOVA (analysis of variance) or two-independent-sample t-test of completely random design data. An LSD method was used when the variance of multiple comparisons between groups was uniform, and a Games-Howell method was used when the variance was not uniform. P<0.05 showed that the difference has statistical meaning. The counting data were checked with $\chi^2$.

Results

1. Effect of the Compound on Spontaneous Activities of Mice

There was no significant change in the number of spontaneous activities in the control group before and after administration, P>0.05. The spontaneous activities of the mice in the low and high dose groups and the positive control group were significantly reduced compared with those before administration, P<0.05, which showed a significant difference; the number of spontaneous activities in the compound groups was significantly different from that of the positive control group. See Table 11.

TABLE 11

Number of Spontaneous Activities in Each Group of Mice (x ± s, n = 10)

| Groups | Before administration (per 10 min) | After administration (per 10 min) |
|---|---|---|
| Blank control group | 99.0 ± 41.37 | 110.5 ± 26.68 |
| Low dose group | 165.5 ± 69.20 | 104.6 ± 42.12△▲▲ |

TABLE 11-continued

Number of Spontaneous Activities in Each Group of Mice (x ± s, n = 10)

| Groups | Before administration (per 10 min) | After administration (per 10 min) |
|---|---|---|
| High dose group | 145.5 ± 82.57 | 84.8 ± 31.69*△▲ |
| Positive control group | 136.6 ± 43.35 | 45.4 ± 34 43**△△ |

*P < 0.05,
**P < 0.01, in comparison with the blank control group.
△P < 0.05,
△△P < 0.01, in comparison with the situation before administration.
▲▲P < 0.01, in comparison with the positive control group.

2. Effect of the Compound on Morphine-Induced Excitability of Mice

As can be seen from Table 12, after morphine administration (sc), the number of activities of the mice in the blank control group was significantly increased compared with that before administration, P<0.01. Early administration of Estazolam, the positive pharmaceutical product, could significantly inhibit the excitability induced by morphine of the mice. The low and high doses of the compound inhibited the excitability induced by morphine to different degrees, compared with the control group, there was significant difference, P<0.01, and compared with the situation before administration, there was also significant difference, P<0.05. See Table 12.

TABLE 12

Effect of the Compound on Morphine-Induced Excitability (x ± s, n = 10)

| Groups | Before administration (Times per min) | After administration (Times per min) |
|---|---|---|
| Blank control group | 164.1 ± 32.41 | 217.5 ± 23.79△△ |
| Low dose group | 191.5 ± 35.53 | 102.0 ± 46.29**△▲ |
| High dose group | 185.4 ± 36.93 | 112.7 ± 23.04**△▲▲ |
| Positive control group | 171.2 ± 38.94 | 67.9 ± 40.31**△△ |

* P < 0.05,
**P < 0.01, in comparison with the blank control group.
△P < 0.05,
△△P < 0.01, in comparison with the situation before administration.
▲▲P < 0.01, in comparison with the positive control group.

3. Effect of the Compound on Amphetamine-Induced Excitability of Mice

As can be seen from Table 13, after amphetamine administration (sc), the number of activities of the mice in the blank control group was significantly increased compared with that before administration, P<0.01. Early administration of Estazolam, the positive pharmaceutical product, could significantly inhibit the excitability induced by amphetamine of the mice. The low and high doses of the compound inhibited the excitability induced by amphetamine to different degrees, compared with the control group, there was significant difference, P<0.01, and compared with the situation before administration, there was also significant difference, P<0.05. See Table 13.

TABLE 13

Effect of the Compound on Amphetamine-Induced Excitability (x ± s, n = 10)

| Groups | Before administration (Times per min) | After administration (Times per min) |
|---|---|---|
| Blank control group | 162.3 ± 40.50 | 233.9 ± 56.45△△ |
| Low dose group | 192.0 ± 45.06 | 130.6 ± 32.11**△▲ |

TABLE 13-continued

Effect of the Compound on Amphetamine-Induced Excitability (x ± s, n = 10)

| Groups | Before administration (Times per min) | After administration (Times per min) |
|---|---|---|
| High dose group | 197.4 ± 39.30 | 132.6 ± 26.26**▲▲▲ |
| Positive control group | 183.7 ± 32.99 | 83.0 ± 40.14**ΔΔ |

*P < 0.05,
**P < 0.01, in comparison with the blank control group.
ΔP < 0.05,
ΔΔP < 0.01, in comparison with the situation before administration.
▲▲P < 0.01, in comparison with the positive control group.

4. Effect of the Compound on Inducing the Mice to Sleep by a Subthreshold Dose of Pentobarbital Sodium The results showed that only two mice in the blank control group fell asleep after being administered (ip) a subthreshold dose of pentobarbital sodium (30 mg/kg). In the positive control group, 18 out of 20 fell sleep. Both the low and high dose groups had mice falling asleep. The number of the mice falling asleep in each group, subjected to $\chi^2$ test, showed that $\chi^2$=26.567, v=3, P=0.000 (both sides), the difference was significant, and it could be considered that the difference among the four experimental groups was significant, wherein the positive control group and the low dose group had the highest number of mice falling asleep. See Table 14 and Table 15.

TABLE 14

Results of Inducing the Mice to Sleep by a Subthreshold Dose of Pentobarbital Sodium (n = 20)

| Groups | Number of the mice showing disappearance of righting reflex (per group) |
|---|---|
| Blank control group | 2 |
| Low dose group | 11 |
| High dose group | 8 |
| Positive control group | 18 |

TABLE 15

Statistical Results of Inducing the Mice to Sleep by a Subthreshold Dose of Pentobarbital Sodium (n = 20)
Chi-Square Tests

|  | Value | df | Asymp. Sig. (2-sided) |
|---|---|---|---|
| Pearson Chi-Square | 26.567$^a$ | 3 | .000 |
| Likelihood Ratio | 30.401 | 3 | .000 |
| Linear-by-Linear Association | 16.620 | 1 | .000 |
| N of Valid Cases | 80 |  |  |

$^a$0 cells (.0%) have expected count less than 5. The minimum expected count is 9.75.

5. Effect of the Compound on Sleeping Duration Induced by Pentobarbital Sodium

As can be seen from Table 16, administration of the compound significantly prolonged the duration of sleep of mice induced by the threshold dose of pentobarbital sodium. The low and high dose groups were significantly different from the control group, P<0.01. The low and high dose groups showed significant difference from the positive control group. See Table 16.

TABLE 16

Effect of the Compound on Sleeping Duration Induced by Pentobarbital Sodiume (x ± s, n = 10)

| Groups | Sleeping duration (min) |
|---|---|
| Blank control group | 25.8 ± 5.01 |
| Low dose group | 39.5 ± 11.46**Δ |
| High dose group | 32.8 ± 9.56*ΔΔ |
| Positive control group | 66.22 ± 13.77** |

**P < 0.01, in comparison with the blank control group.
ΔΔP < 0.01, in comparison with the positive control group.

Conclusion

The results showed that the compound could reduce the number of spontaneous activities of mice, inhibit the increase of excitability induced by morphine and amphetamine, increase the number of mice sleeping induced by the subthreshold dose of pentobarbital sodium, and prolong the sleeping duration of mice induced by the threshold dose of pentobarbital sodium. The compound had sedative and hypnotic effects, but was weaker than the positive drug Estazolam.

Experimental Study on Self-Dependence of the Compound

According to the technical requirements of special toxicity test of new drugs, the compound was tested for drug dependence. The results of the naloxone-induced withdrawal test of mice and rats showed that no obvious withdrawal symptoms were observed after the administration of the compound. The results of the place preference test showed that the mice had no tendency of psychological dependence after being administered the compound. This study showed that the compound had no physical and psychological dependence potential and had no dependence characteristics.

Object of Experiment

It's an object of the experiment to provide an experimental basis and related reference information for safe application of the compound by evaluating the dependence potential of the compound through a rat body dependence test and a mouse psychological dependence test to predict the addiction human may have thereto.

Materials for Experiment

Test Pharmaceutical Products, i.e., the compound of the present application

Name: the compound (raw medicinal powder)
Provided by: Guangxi Jiufu Biotechnology Co., Ltd
Batch Number: 20160518
Storage conditions: 4° C. in refrigerator
Preparation method: dissolve to the desired concentration by heating with vegetable oils, and prepare prior to the experiment.

Instrument for Experiment

A conditioned place preference box was composed of black and white cuboids (30 cm×15 cm×15 cm), a movable partition plate is arranged in the middle of the box body to divide the box into two cuboids of the same volume, and the rat and mice can freely move from one cuboid to another when the partition plate is removed. Inner surfaces of one cuboid of the box body except the glass panel is painted black, the bottom plate is made to be a rough surface by using a soft blanket, the other cuboid of the box body except the glass surface is painted white, the bottom plate is made to be a smooth surface, and the whole experimental box has visual and tactile cues.

Laboratory Animals for Experiment

Sprague-Dawley (SD) rats, SPF grade, male, 8 week old, grade SPF, weighing 180-220 g, were provided by the Laboratory Animal Center of Southern Medical University, animal qualification number: SCXK YUE 2011-0015.

Kunming mice, 7 weeks old, weighing 18-22 g, half males and half females, provided by the Laboratory Animal Center of Southern Medical University. Grade SPF, animal qualification number: SCXK YUE 2011-0015.

After the animals were purchased by the laboratory, the males and females were separated. The animals were free to drink and eat, and the feed for them was granules produced by the Laboratory Animal Center of Southern Medical University. They were kept under the following conditions: temperature 24±2° C., humidity (60±5)%.

Methodology

1. Physical Dependence Test 1.1 Induced Withdrawal Test for the Rats

Thirty healthy SD rats, half males and half females, were randomly divided into three groups: a morphine control group, a compound group and a negative control group, 10 for each group. The morphine control group and the compound group were administered according to a dose increasing method, and the morphine control group was given (sc) morphine hydrochloride twice a day. The dosage of morphine was increased from 5 mg·kg$^{-1}$ to 60 mg/kg each time according to the dose increasing principle and this continued to day 7. The compound group was administered (ig) twice a day according to the dose increasing principle, at daily doses of 0.5, 1.0, 1.5, 2.0, 2.5, 3.0 g/kg. The dose was increased every day from 0.5 g/kg to 3.0 g/kg on day 6 which was adopted the same on day 7. The negative control group was given (ig) the same volume of vegetable oil per day at the same time and for the same times as the compound group. On day 8, the rats in each group were given naloxone (5 mg/kg, ip) to induce withdrawal, and the withdrawal status of the rats within 30 min and the weight change one hour before and after the inducement were observed. The evaluation criteria of withdrawal symptoms of rats were established by referring to the Tomoji Yanagita evaluation criteria and our pre-experimental results (see Appendix Table 17). The withdrawal scores and weight loss values of each group of rats were statistically processed. Weight loss value=weight before inducement−weight after inducement.

1.2 Induced Withdrawal Test for the Mice

Thirty healthy SD rats, half males and half females, were randomly divided into three groups: a morphine control group, a compound group and a negative control group, 10 for each group. The morphine control group and the compound group were administered according to a dose increasing method, and the morphine control group was given sc morphine hydrochloride twice a day (8:00 am, 8:00 pm). The daily doses were 25, 50, 75, 100, 125, 150 mg/kg according to the dose increasing principle, increased day by day, reached 150 mg/kg on day 6 which was adopted the same on day 7. The compound group was administered (ig) twice daily (8:00 am, 8:00 pm) at daily doses of 0.6, 1.2, 1.8, 2.4, 3.0, 3.6 g/kg. The dose increased every day from 0.6 g/kg to 3.6 g/kg on day 6 which was adopted the same on day 7. The negative control group was given (ig) the same volume of vegetable oil every day at the same time and for the same times as the compound group. On day 7, naloxone (8 mg/kg, ip) was given to each group of mice to induce withdrawal. The jump reaction within 30 min and weight change one hour before and after inducement were observed. Weight loss value=weight before inducement−weight after inducement.

2. Psychological Dependence Test 2.1 Conditioned Place Preference Test of Mice

Mice were tested for natural preference one day prior to dosing to eliminate mice with significant preference on one side of the box and to exclude the effects of unconditioned place preference on the experimental results.

Thirty Kunming mice, half males and half females, were randomly divided into three groups: a morphine control group (9 mg/kg), a compound group and a negative control group, 10 for each group. Each group of animals was administered twice daily at an interval of 8 hours (8:00, 16:00). The negative control group was given (ig) vegetable oil (30 ml/kg) and normal saline (30 ml/kg) once each, the morphine group was given sc morphine hydrochloride and normal saline (30 ml/kg) once each, and the compound group was given (ig) the extract liquid (0.4 g/kg) and normal saline (30 ml/kg) once each. The mice were placed in the white cuboid, which was the non-preferred side, after administration, and placed in the black cuboid, which was the preferred side, after administration of normal saline. The mice were kept in the box for 45 min, trained for 6 days. The place preference test was performed 24 h after the last administration. The partition plate of the preferred cuboid was removed, the mice were placed in the middle of the box one by one and observed for 15 minutes, and the duration of each of the mice staying in each cuboid was recorded on the basis of the positions of their heads.

3. Statistical Processing

The experimental data were expressed as x±s. The statistical software SPSS 13.5 was used to carry out one-way ANOVA (analysis of variance) or two-independent-sample t-test.

Results

1. Results of the Induced Withdrawal Test of Rats

After naloxone inducement, withdrawal symptom scores and weight loss of the morphine control group rats were significantly higher than those of the negative control group (P<0.01), indicating that the morphine group rats developed obvious physical dependence. The rats in the compound group were treated with naloxone for 7 consecutive days according to the dose increasing method, without obvious withdrawal symptoms, and there was no significant difference in the score and weight loss between the rats in the compound group and the negative control group (P>0.05); but there was a significant difference between the compound group and the morphine control group, P<0.01. See Table 18.

TABLE 18

Induced Withdrawal Symptoms Score and Body Weight Change of Each Group of Rats ($\bar{x} \pm s$, n = 10)

| Groups | Induced withdrawal symptom score | Weight loss (g) |
| --- | --- | --- |
| Negative control group | 2.9 ± 2.24 | 0.2 ± 3.39 |
| Morphine control group | 76.9 ± 14.53** | 9.5 ± 3.62** |
| High dose the compound group | 7.2 ± 3.37## | 1.1 ± 2.46## |

**P < 0.01, in comparison with the blank control group;
P < 0.01, in comparison with the morphine group.

2. Results of the Induced Withdrawal Test of Mice

In the morphine control group, after sc morphine hydrochloride administration, all the mice showed tail erecting reaction and excitatory movement. The negative control group mice were given normal saline and had no abnormal performance thereafter. The mice in the compound administration group were administered according to the dose increasing method and then were quiet without tail erecting reaction or excitatory movement like the morphine group. After 7 days of naloxone inducement, the morphine control group showed significant jump reaction and weight loss compared with negative control group (P<0.01). After naloxone was given to the compound group, occasionally there were 1 or 2 jumps found in individual mice, the weight loss was not significant, and there was no significant difference between the compound group and the negative control group (P>0.05), but there was significant difference between the compound group and the morphine dependent group (P<0.01). See Table 19.

TABLE 19

Number of Jumps and Weight Loss for Each Group of Mice ($\bar{x} \pm s$, n = 10)

| Groups | Number of jumps | Weight loss (g) |
|---|---|---|
| Negative control group | 0.33 ± 0.67 | 0.15 ± 0.16 |
| Morphine control group | 64.10 ± 15.29** | 0.57 ± 0.25** |
| Compound group | 1.70 ± 2.79## | 0.12 ± 0.13## |

**$P < 0.01$, in comparison with the blank control group;
$P < 0.01$, in comparison with the morphine group.

3. Results of Conditioned Place Preference Test of Mice

After 6 days of administration, the duration of the mice in the morphine control group staying in the companion box was significantly longer than that before administration (P<0.05), and also significantly longer than that of the negative control group (P<0.01), indicating that morphine induced significant place preference of mice. In the compound group, the duration of the mice staying in the companion box was not significantly prolonged 6 days after administration, having no significant difference compared with that before administration (P>0.05), and there was no significant difference compared with the negative control group (P>0.05) either, indicating no rewarding or aversive effect was generated in the mice regarding the compound. See Table 20.

TABLE 20

Conditioned Place Preference Effects of Each Group of Mice ($\bar{x} \pm s$, n = 10)

| | Duration of mice staying in companion box (s) | |
|---|---|---|
| Groups | Before administration | After administration |
| Negative control group | 337.5 ± 74.08 | 360.9 ± 75.54 |
| Morphine control group | 362.5 ± 67.51 | 578.6 ± 136.83**Δ |
| Compound group | 334.8 ± 94.96 | 385.2 ± 188.16## |

**$P < 0.01$, in comparison with the blank control group.
$P < 0.05$,
$P < 0.01$, in comparison with the morphine model group;
Δ$P < 0.05$, in comparison with the situation before administration.

Conclusion

Drug dependence is an adaptive response to drugs, which includes physical (physiological) dependence and psychological dependence. This study was conducted to evaluate the physical and psychological dependence of the compounds by using currently internationally recognized and commonly used drug-dependent animal tests. The results showed that the morphine group had obvious withdrawal response to naloxone, but the compound group had no withdrawal response. Weight loss is an important sign of opioid addiction and withdrawal. Morphine-dependent rats and mice were accompanied by significant weight loss during withdrawal, while no significant weight loss was observed in the compound group. These results all indicated that the compound does not have physical-dependent properties.

Conditioned place preference test is a simple and effective method to evaluate the potential of drug dependence. The results showed that the compound itself did not produce reward effect or aversive effect in mice, and the mice did not develop conditioned place preference due to the compound, suggesting that the drug does not have psychological-dependent properties.

In summary, the results of this study indicated that the compound has no physical or psychological-dependent potential.

APPENDIX TABLE 17

Table of Records of Withdrawal Symptoms of Rats

| Countable symptoms | Times of occurrence in 15 minutes | | | | |
|---|---|---|---|---|---|
| shaking like a wet dog | | | | | |
| Stereotyped acts | | | | | |
| Erecting | | | | | |
| Jumping | | | | | |
| Uncountable symptoms | 1-3 min | 4-6 min | 7-9 min | 10-12 min | 13-15 min |
| Abnormal posture (+, −) | | | | | |
| Pilus erection (+, −) | | | | | |
| Tooth tremor (+, −) | | | | | |
| Rapid respiration (+, −) | | | | | |
| Ptosis (+, −) | | | | | |
| Irritability (+, −) | | | | | |
| Diarrhoea | Soft feces (4), shapeless feces (8), none (0) | | | | |
| Lacrimation | Slight (1), obvious (2), none (0) | | | | |
| Rhinorrhea | Slight (1), obvious (2), none (0) | | | | |
| Salivation | Slight (2), obvious (3), none (0) | | | | |

Experiment of Acute Toxicity of the Compound in Mice

Object of Experiment

It's an object of the experiment to provide an experimental basis for the safety evaluation of the compound by an oral acute toxicity test of mice to observe the acute toxicity effect of the compound on mice.

Pharmaceutical Products for Experiment

The compound, provided by Guangxi Jiufu Biotechnology Co., Ltd., batch number: 20160518. The compound was dissolved to a concentration of 10% by heating with vegetable oil, and prepared prior to the experiment.

Laboratory animal for Experiment

Kunming mice, half males and half females, weighing 18-22 g, were provided by the Laboratory Animal Center of Southern Medical University. Grade SPF, animal qualification number: SCXK YUE 2011-0015.

The mice were divided into males and females, housed 5 per cage. Cages and trays for the mice were cleaned and disinfected before use. The mice had their freedom to drink and eat, and the feed for them was granules produced by the Laboratory Animal Center of Southern Medical University. The mice were kept under the following conditions: temperature 24±2° C., humidity (60±5)%, illumination period 12 h:12 h. Padding for the rats was replaced once a week, and their drinking bottles were replaced and washed once a day. The breeding room was disinfected regularly and managed by a special person.

Test Control

Blank control group: administered (ig) with the same volume of vegetable oil.

Methodology

Forty Kunming mice, half males and half females, were randomly divided into a test group and a control group, 20 for each group. The test group was given 10% the compound, 0.3 ml/10 g per dose, and the control group was given the same volume of vegetable oil. Each group was administered (ig) twice a day at 8:00 and 18:00, respectively, and fasting was completed three hours after the administration (ig). All the mice received the same volume of 0.3 ml/10 g per dose, amounting to 6 g/kg BW over 24 hours. The mice were given free access to water and food after administration. The body weight, food intake, water intake, general physiological indicators, behaviors and activities, psychological status and survival status were recorded for 14 days in consecutive, 3 times a day, after several times of observation within the 24 hours that followed the administration.

Results

In this experiment, the test liquid was given (ig) twice a day, the psychological state and activities of the mice in the test group and the control group were consistent after the administration. There was no obvious abnormal behavior found in the test group. After 14 days of observation, none of the test animals died and no toxic reaction occurred. The mice in both groups showed no abnormal performance, ended up with smooth fur, normal diet, normal stool and urine, no abnormal secretion in eyes and nose, and no congestion in mucous membrane. After putting them to death, no abnormality was found in heart, liver, spleen, lung or kidney by visual observation.

There was no significant difference in body weight between the test group and the control group, P>0.05. See Table 21.

TABLE 21

Changes in Body Weight of Each Group of Mice (x ± s, n = 20)

| Groups | Gender | Weight before dosing/g | Weight after dosing/g | Weight change/g |
|---|---|---|---|---|
| Test group | Female | 20.93 ± 1.61 | 24.99 ± 1.59 | 4.06 ± 2.34 |
| | Male | 20.73 ± 1.79 | 26.60 ± 0.87 | 6.13 ± 1.46 |
| Control group | Female | 21.68 ± 1.23 | 24.14 ± 1.11 | 2.46 ± 0.56 |
| | Male | 20.29 ± 2.10 | 27.75 ± 0.69 | 7.46 ± 2.42 |

Conclusion

In this experiment, the compound of the maximum volume and concentration were given (ig) to mice, no death occurred, LD50 could not be detected. Therefore, the mice were given (ig) the dose of 3 g/k twice within 24 hours by using the maximum dose method. After 14 days of observation, none of the test animals died and no toxic reaction occurred. The maximum dose given the mice was measured to be 6 g/kg, corresponding to 300 times the daily dose per the same body weight for a human adult in clinic. The compound had no obvious acute toxicity effect on mice after oral administration, suggesting that the compound was low in toxicity and high in use safety.

Note: doses for an adult: 0.7 g/day, twice a day, 1.4 g/day, calculated as 70 kg per person, dose for an adult: 0.02 g/kg.

Summary of Experimental Study on Pharmacodynamics of the Compound in Drug Withdrawal Through the research work of experiments I~VII, the results showed that the compound of the present application has a certain detoxification treatment effect on withdrawal symptoms of morphine-dependent rats; the compound has a certain sedative and hypnotic effect, which could inhibit the excitability of mice induced by morphine and amphetamine; the results also showed that the compound had no physical or psychological dependence potential and no dependence characteristics; LD50 was also not detected. None of the animals tested died at a maximum dose of 6 g/kg per mouse, equivalent to 300 times the dose for a human adult (0.02 g/kg for an adult), indicating that it was safe in terms of acute toxicity.

However, the compound had no obvious analgesic effect.

In conclusion, the compound was safe in terms of acute toxicity, generated no physical dependence, had an inhibitory effect on the excitability of mice induced by morphine and amphetamine, and had a detoxification treatment effect on withdrawal symptoms of morphine-dependent rats, therefore, the compound is a pharmaceutical product for drug withdrawal worthy of further development.

The invention claimed is:

1. A method for preparing a compound, comprising the following steps:
    S1: pulverizing Limax to obtain Limax powder;
    S2: putting the Limax powder into a supercritical $CO_2$ extractor and conducting extraction to obtain an extract;
    S3: adding the extract, potassium hydroxide, and water to a reactor in a weight ratio of "extract:potassium hydroxide:water=1:1:1.5", mixing evenly, and heating and stirring to produce a saponification reaction to obtain a reaction solution A;
    S4: adding the reaction solution A to an organic solvent for extraction, separating the organic solvent layer, washing with water until the water washed solution becomes neutral, separating the organic solvent layer, and recovering the organic solvent under reduced pressure to obtain a thick paste A;
    S5: adding methanol to thick paste A, heating to dissolve, filtering, leaving a filtrate to cool, standing, crystallizing, and reserving a mother liquor; and
    S6: subjecting the crystals to preparative medium-pressure liquid phase separation to obtain the compound;
    wherein the compound having a structure of:

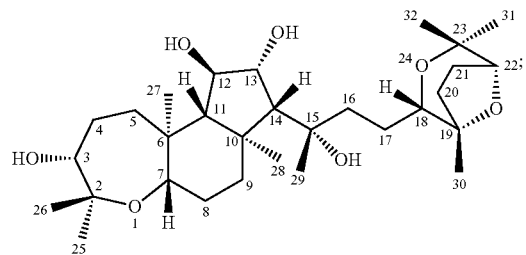

wherein the liquid phase conditions are as follows: reversed-phase C18 column, and solvent system: methanol:acetonitrile:isopropanol:water (70:20:6:4).

2. The method for preparing the compound according to claim 1, wherein the organic solvent comprises one or two of ethyl ether, ethyl acetate, and n-butanol.

3. The method for preparing the compound according to claim 1, wherein the conditions for supercritical $CO_2$ extraction comprise: pressure: 25 KPa, temperature: 65° C., flow: 400-500 PV, and extraction time: 4 h.

4. The method for preparing the compound according to claim 1, further comprising the following steps: taking the mother liquor of S5, adding water in a ratio of methanol: water (8:2), heating under reflux, and separating a black oil, filtering with the methanol solution, recovering the methanol, drying, and adding trichloromethane into the residue, heating to dissolve, cooling, standing to precipitate crystals, and filtering to obtain the crystals; washing with a small amount of trichloromethane, drying, adding methanol, heating to dissolve, cooling, precipitating crystals, filtering, and drying to obtain the compound.

5. A method for preparing a compound, comprising the following steps:
   T1: pulverizing Limax to obtain Limax powder;
   T2: putting the Limax powder into a multi-functional extraction tank, adding an organic solvent, extracting under reflux conditions, filtering, and recovering the organic solvent from the extraction solution under reduced pressure to obtain a thick paste B;
   T3 adding thick paste B, potassium hydroxide and water to a reactor in a weight ratio of "extract:potassium hydroxide:water=1:1:1.5", mixing evenly, and heating and stirring to produce a saponification reaction to obtain a reaction solution B;
   T4: adding the reaction solution B to an organic solvent for extraction, separating an organic solvent layer, washing with water until the water washed solution becomes neutral, separating the organic solvent layer, and recovering the organic solvent under reduced pressure to obtain a thick paste C;
   T5: adding methanol to thick paste C, heating to dissolve, filtering, leaving a filtrate to cool, letting it stand, crystallizing, and reserving a mother liquor; and
   T6: subjecting the crystals to preparative medium-pressure liquid phase separation to obtain the compound; wherein the compound having a structure of:

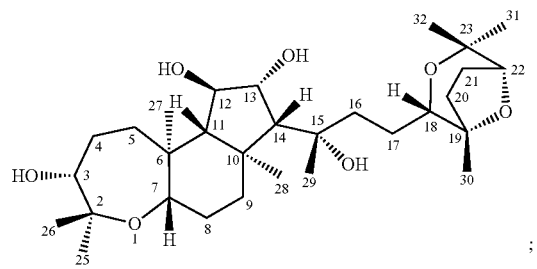

wherein the liquid phase conditions are as follows: reversed-phase C18 column, and solvent system: methanol:acetonitrile:isopropanol:water (70:20:6:4).

6. The method for preparing the compound according to claim 5, wherein the organic solvent comprises one or two of n-hexane, ethanol, methanol, acetone, trichloromethane, oil, gasoline, petroleum ether, n-butanol, ethyl ether, and ethyl acetate.

7. The method for preparing the compound according to claim 5, further comprising the following steps: taking the mother liquor of T5, adding water in a ratio of methanol: water (8:2), heating under reflux, and separating a black oil, filtering with the methanol solution, recovering the methanol, drying, and adding trichloromethane into the residue, heating to dissolve, cooling, standing to precipitate crystals, and filtering to obtain the crystals; washing with a small amount of trichloromethane, drying, adding methanol, heating to dissolve, cooling, precipitating crystals, filtering, and drying to obtain the compound.

* * * * *